US011709861B1

(12) United States Patent
Clark et al.

(10) Patent No.: US 11,709,861 B1
(45) Date of Patent: Jul. 25, 2023

(54) ACCESS ENHANCEMENTS FOR NETWORK BASED INTERACTIVE PLANNING SYSTEMS

(71) Applicant: Aptima, Inc., Woburn, MA (US)

(72) Inventors: Timothy Clark, Dallas, TX (US); Christopher Jenkins, Orlando, FL (US); Gabriel Ganberg, Mountlake Terrace, WA (US); Vinay Bharadwaj, Waltham, MA (US)

(73) Assignee: Aptima, Inc., Woburn, MA (US)

( * ) Notice: Subject to any disclaimer, the term of this patent is extended or adjusted under 35 U.S.C. 154(b) by 62 days.

(21) Appl. No.: 17/091,907

(22) Filed: Nov. 6, 2020

Related U.S. Application Data

(60) Provisional application No. 62/931,237, filed on Nov. 6, 2019.

(51) Int. Cl.
*G06F 16/00* (2019.01)
*G06F 16/27* (2019.01)
(Continued)

(52) U.S. Cl.
CPC .......... *G06F 16/27* (2019.01); *A63B 24/0075* (2013.01); *G06F 16/2379* (2019.01);
(Continued)

(58) Field of Classification Search
CPC .... G06F 16/27; G06F 16/2379; G06F 16/252; A63B 24/0075; A63B 2225/20; G16H 20/30; H04L 67/1095
See application file for complete search history.

(56) References Cited

U.S. PATENT DOCUMENTS 6,708,221 B1 * 3/2004 Mendez ............... H04L 67/2876
709/248
7,487,472 B2 * 2/2009 Mantena ................. H04L 63/02
716/126

(Continued)

OTHER PUBLICATIONS

Bullock, S. H., Jones, B. H., Gilchrist, J., & Marshall, S. W. (2010). "Prevention of physical training-related injuries: recommendations for the military and other active populations based on expedited systematic reviews". Am J Prev Med, 38(1), S156-S181. 26 pgs.

(Continued)

*Primary Examiner* — Alexander Khong
(74) *Attorney, Agent, or Firm* — John J. Brooks, III

(57) ABSTRACT

An interactive planning system is provided to allow a user to create and manage plans in online, offline, and intermittent connectivity environments. In some embodiments, the interactive planning system comprises a mobile, web-based application with an in-browser database configured to allow the user to create and manage plans in an offline environment and synchronize the plan when online connectivity is restored. In some embodiments, the interactive planning system comprises a fitness planning system configured to allow users to create and manage physical fitness plans in online, offline, and intermittent connectivity environments; to provide instructors the ability to enter fitness plan attributes, detail focus areas and timeframe for fitness plans; to provide instructors the ability to highlight macro-level phases to inform plan analytics; and to provide an ability to share programs to groups.

20 Claims, 23 Drawing Sheets

(51) Int. Cl.
  *G06F 16/25* (2019.01)
  *G16H 20/30* (2018.01)
  *A63B 24/00* (2006.01)
  *G06F 16/23* (2019.01)
  *H04L 67/1095* (2022.01)
(52) U.S. Cl.
  CPC ............ *G06F 16/252* (2019.01); *G16H 20/30* (2018.01); *A63B 2225/20* (2013.01); *H04L 67/1095* (2013.01)

(56) References Cited

U.S. PATENT DOCUMENTS

| | | | |
|---|---|---|---|
| 9,773,051 B2* | 9/2017 | Smith | G06F 16/176 |
| 2013/0162444 A1* | 6/2013 | Boulanger | H04Q 9/00 340/870.03 |
| 2015/0379037 A1* | 12/2015 | Pimprikar | G06F 21/6227 707/610 |
| 2016/0342670 A1* | 11/2016 | Smith | G16H 10/60 |
| 2016/0344808 A1* | 11/2016 | Smith | H04L 67/12 |
| 2017/0169403 A1* | 6/2017 | Zhang | G06Q 20/065 |
| 2019/0118066 A1* | 4/2019 | Cardona | A63B 24/0062 |
| 2019/0304593 A1* | 10/2019 | Shiibashi | G16H 80/00 |
| 2019/0361463 A1* | 11/2019 | Nelson | G06F 16/9537 |

OTHER PUBLICATIONS

Hauret, K. G., Jones, B. H., Bullock, S. H., Canham-Chervak, M., & Canada, S. (2010). Musculoskeletal injuries: description of an under-recognized injury problem among military personnel. Am J Prev Med, 38(1), S61-S70. 10 pgs.

US Army. (2011). "Prevention and Control of Musculoskeletal Injuries Associated with Physical Training." Technical Bulletin Medical (TB Med) 592. Washington, DC, USA. 87 pgs.

Altarac, M., Gardner, J. W., Popovich, R. M., Potter, R., Knapik, J. J., & Jones, B. H. (2000). Cigarette smoking and exercise-related injuries among young men and women. Am J Prev Med, 18(3), 96-102. 7 pgs.

Fowler, Martin. "Event Sourcing". Accessed Sep. 20, 2018 at https://martinfowler.com/eaaDev/EventSourcing.html. 21 pgs.

Lepage, Pete. "Storage for the web". Accessed Sep. 20, 2018 at https://developers.google.com/web/fundamentals/instant-and-offline/web-storage/offline-for-pwa. 10 pgs.

Witalec, Sebastian. "Apps that Work Natively on the Web and Mobile." Accessed Sep. 20, 2018 at https://blog.angular.io/apps-that-work-natively-on-the-web-and-mobile-9b26852495e7. 10 pgs.

Fragmentary Order 4 (Implementation) to Marine Corps Force Integration Campaign Plan. Quantico, VA, USA 2015. 41 pgs.

(DTM)-18-001 Establishment of the Secretary of Defense Close Combat Lethality Task Force (Mar. 16, 2018), Attachment 2, 7 b.2. Quantico, VA, USA. 2015. 14 pgs.

Cross, M. J., Williams, S., Trewartha, G., Kemp, S. P. T., & Stokes, K. A. (2016). The Influence of In-Season Training Loads on Injury Risk in Professional Rugby Union. International Journal of Sports Physiology and Performance, 11(3), 350-355. London, England. 23 pgs.

Gabbett, T. J., Hulin, B. T., Blanch, P., & Whiteley, R. (2016). High training workloads alone do not cause sports injuries: how you get there is the real issue. Br J Sports Med, 50(8), 444-445. https://doi.org/10.1136/bjsports-2015-095567 . Doha, Qatar. 4 pgs.

Hulin, B. T., Gabbett, T. J., Blanch, P., Chapman, P., Bailey, D., & Orchard, J. W. (2014). Spikes in acute workload are associated with increased injury risk in elite cricket fast bowlers. Br J Sports Med, 48(8), 708-712. https://doi.org/10.1136/bjsports-2013-092524. London, England. 7 pgs.

Hulin, Gabbett, Lawson, Caputi, Sampson. "The acute:chronic workload ratio predicts injury: high chronic workload may decrease injury risk in elite rugby league players" Wollongong, New South Wales. 7 pgs.

MDN web docs. "Web App Manifest". Accessed Sep. 20, 2018 at https://developer.mozilla.org/en-US/docs/Web/Manifest. 15 pgs.

Relational Database Service. Accessed Sep. 20, 2018. Retrieved Oct. 30, 2020 from https://aws.amazon.com/rds/. 13 pgs.

PostgreSQL for Azure. Accessed Sep. 20, 2018. Retrieved Oct. 30, 2020 at https://docs.microsoft.com/en-us/azure/postgresql/overview, pp. 1-361, 361 pgs.

PostgreSQL for Azure. Accessed Sep. 20, 2018. Retrieved Oct. 30, 2020 at https://docs.microsoft.com/en-us/azure/postgresql/overview, pp. 362-697, 361 pgs.

Twelve Factor App Principles. Accessed Sep. 20, 2018 at https://12factor.net/. Retrieved on Oct. 30, 2020. 28 Pgs.

Angular. Accessed Sep. 20, 2018 at https://angular.io/. Retrieved on Oct. 30, 2020. 2 pgs.

Progressive Web Apps. Accessed Sep. 20, 2018 at https://developers.google.com/web/progressive-web-apps/. Retrieved on Oct. 30, 2020. 3 pgs.

\* cited by examiner

```json
{
  "exercise_program_id": "93da2a12-296a-4f8a-ae79-8f1bad97939a",
  "exercise_program_version": 1,
  "exercises": [],
  "id": "5f82c2a1-19b6-441c-9306-b968eeb88d2c",
  "name": "Seed plan",
  "num_weeks": 12,
  "phases": [
    {
      "color": "purple",
      "end_day": 6,
      "end_week": 10,
      "id": "0ac67aaf-ca01-4b21-8118-4cfd7ad3226b",
      "name": "Hypertrophy",
      "start_day": 0,
      "start_week": 0
    },
    {
      "color": "green",
      "end_day": 6,
      "end_week": 11,
      "id": "45f17819-eb92-41fa-b146-d97397ca70c1",
      "name": "Power",
      "start_day": 0,
      "start_week": 1
    }
  ],
  "start_date": "01/01/2019",
  "type": "Plan",
  "version": 1,
  "workouts": [
    {
      "id": "6de3866c-b425-402c-9850-3512ab241f63",
      "name": "Plan Day 0",
      "schedule": {
        "day": [
          0
        ],
        "week": [
          0,
          1
        ]
      },
      "tiers": [
        {
          "id": "46827046-d906-4252-9b69-263ddb6e9699",
          "name": "Agility",
          "notes": "",
          "order": 3,
          "rows": [
            {
              "exercise_id": "34d9217b-0748-4e01-b784-6c2dceea0ae1",
              "exercise_name": "Ladder Skiers",
              "order": 1,
              "parameter_selections": {
                "sets": "2"
              }
            }
```

FIG. 10A

MOS SPECIFIC PHYSICAL STANDARDS

| Task | MOS | Task Description | Standard |
|---|---|---|---|
| Casualty Evacuation | All GCE MOSs & LAAD | While wearing a fighting load and carrying a service rifle, sprint 25 meters to a simulated casualty, evacuate the casualty 25 meters | 54 sec |
| MK-19 Lift | All GCE MOSs & LAAD | Lift the MK-19 heavy machinegun from the deck to overhead height. | Pass |
| Scale a Wall | 03xx | Scale a 56" wall unassisted while wearing the Fighting Load and carrying a service rifle | 30 sec |
| 20km Hike | 0302, 0311, 0331, 0341, 0351, 0352 | March 20 km with MOS specific weapons & equipment while wearing the fighting load | 5 hours |
| Rush 300m to Objective | 0302 0311 | While wearing a fighting load and carrying a service rifle, run/rush for 300 meters through a course with an agility network | 3 min 56 sec |
| 200m Movement as MG Ammo Bearer | 0331 | While wearing a fighting load and carrying a service rifle, Spare barrel bag and two ammo cans, run/rush for 200 meters through a course with an agility network | 2 min 11 sec |
| 200m Movement w/ 60mm Mortar | 0341 | While wearing a fighting load and carrying a service rifle, and a 60mm mortar in hand-held mode, run/rush for 200 meters through a course with an agility network | 1 min 45 sec |
| 200m Movement w/ SMAW | 0351 | While wearing a fighting load and carrying a service rifle, and a SMAW, run/rush for 200 meters through a course with an agility network | 1 min 40 sec |
| Breach Door w/ Battering Ram | 0302 0351 | While wearing a fighting load and carrying a service rifle, breach a door with a battering ram | 14 sec |
| 200m Movement w/ Javelin | 0352 | While wearing a fighting load and carrying a service rifle, and a Javelin, run/rush for 200 meters through a course with an agility network | 1 min 43 sec |
| Disassemble/ Assemble M242 25mm Gun | 0303 0313 | Disassemble/Assemble the M242 25mm automatic gun by manipulating the receiver and feeder | 3 min 21 sec |
| LAV CASEVAC | 0303, 0313, 2147 | Clean & press Olympic bar with total weight of 115 lbs. (Surrogate) | Pass |
| Lift LAV Towbar | 0303, 0313, 2147 | Deadlift & hold Olympic bar with total weight of 150 lbs. at knuckle height for 30 seconds (Surrogate) | Pass |

FIG. 11

| Plan Characteristic | Description |
|---|---|
| Usage | |
| Rating | 5 star rating system - allow Marines to provide ratings; track ratings by plan completion status |
| Comments | Verified review; also track comments by plan completion status |
| Number enrolled | How many units/people are enrolled in the specific plan right now? |
| Effectiveness | |
| Subjective description | Free text description from plan author describing purpose of plan and for whom it was designed |
| Goal | What will you get by selecting this plan? What is the expected outcome? |
| Verification for particular goal | Is this trustworthy? Does it do what it's supposed to do? |
| Average PFT score change | Average PFT score increase for individuals who completed this plan |
| Average weight change | For each gender, average weight change; if enough data, allow filtering by height ranges too |
| Logistics | |
| Objective description | Free text description from plan author describing the rhythm of the plan (e.g., 3 days/week with 1-2 day(s) off in between workouts, or initial emphasis on foundational movements with increasing strength training at end) |
| Duration | Number of weeks |
| Average playcard length | Average length of each workout session |
| Average days/week | Average number of days per week |
| Resources needed | Equipment needed (bodyweight vs. full gym) and/or space requirements (indoor/outdoor, pool, circuit) |
| Group/individual recommendation | If plan is recommended for groups vs. individuals (group plans tend to have time-based or paired exercises) |
| Training level | Beginner, intermediate, advanced |
| Injury recommendation | Is this plan good for someone recovering from a knee injury? Shoulder injury? |

FIG. 12

ACCESS ENHANCEMENTS FOR NETWORK BASED INTERACTIVE PLANNING SYSTEMS

CROSS-REFERENCE TO RELATED APPLICATIONS

This application claims the benefit of U.S. App. No. 62/931,237, filed on Nov. 6, 2019, entitled "FITNESS PLANNING SYSTEM," the entire contents of which is incorporated herein by reference.

STATEMENT REGARDING FEDERALLY SPONSORED RESEARCH OR DEVELOPMENT

This invention was made with Government support under Contract No. N68335-17-C-0044 awarded by the U.S. Navy Office of Naval Research. The Government has certain rights in the invention.

REFERENCE TO SEQUENCE LISTING, A TABLE, OR A COMPUTER PROGRAM LISTING COMPACT DISC APPENDIX

Not Applicable.

BACKGROUND OF THE INVENTION

1. Field of the Invention

This invention relates to planning systems, in particular a data network based interactive planning system to be used in both on-line and off-line environments.

2. Background

Training-related musculoskeletal injury (MSK-I) continues to significantly impact the health and readiness of DoD Service Members. Numerous committees have been stood up to research and report on the impact these injuries pose to operational readiness. Specifically, research from the Military Training Task Force of the Defense Safety Oversight Council shows us that: "Injury is undisputedly the leading health and readiness threat to the armed forces. Injuries are the leading cause of service member hospitalizations and outpatient visits, many resulting in preventable discharges, and account for over 25 million limited duty days DoD-wide annually."

Other research provides insights into the reasons for injuries, such as cumulative effects from microtraumas presented through overuse, overexertion, repetitive movements, forceful actions, vibration forces, extreme joint positions, and prolonged static postures. Overall, we see a large number of inflammation/pain cases leading to significant man-hours lost. In terms of training activities leading to injury, an Army Technical Bulletin on Prevention and Control of Musculoskeletal Injuries Associated with Physical Training points to such factors as gender (females more likely to be injured than males), low aerobic fitness, high/low extremes in flexibility, low physical activity prior to (Army) Basic Combat Training, and smoking as leading causes of musculoskeletal injury, either acute or long-term. Other sources provide us information on injury prevention strategies, and assessments of their effectiveness on military populations. Many of these assessments can trace to the adequacy of existing physical training practices and workflows, offering a point of intervention to address these issues.

The United States Marine Corps (USMC) has responded to high numbers of musculoskeletal injuries sustained during physical training by creating a Force Fitness Division (FFD) in 2016, with a mission to be "the service-level division for development and implementation of policy, standards, guidance, and reporting of all matters related to general physical fitness, occupational fitness, performance nutrition, body composition, martial arts, water survival, and sports medicine/injury prevention based on requirements and direction from higher headquarters."

As part of the FFD, Force Fitness Instructors (FFIs) create physical training plans for their assigned Marine units. The FFD, as can be expected with any new organization, initially lacked tools and automated methods for evaluating plan effectiveness, personalizing and adapting training according to individual Marine characteristics, and sharing domain knowledge and resources illustrating the proper form and techniques for conducting exercises. In addition, it remains difficult for individual Marines to communicate with FFIs, Athletic Trainers (ATs), and Strength and Conditioning Coaches (SCCs) about potential exercise modifications for those with prior injuries or specific physiological needs. To be effective, this knowledge must scale to the entire Fleet.

Additional justification and support for increasing the focus on physical readiness can be found in the principles underlying the DoD's drive to improve the performance and resilience of Infantry warfighters. The Close Combat Lethality Task Force (CCLTF) was established in 2018 to provide institutional backing and funding toward these goals.

BRIEF SUMMARY OF THE INVENTION

The following summary is included only to introduce some concepts discussed in the Detailed Description below. This summary is not comprehensive and is not intended to delineate the scope of protectable subject matter, which is set forth by the claims presented at the end.

In one example embodiment, a processor based interactive planning system is provided comprising: a planner subsystem; a mobile subsystem; the planner subsystem comprising a user profile database, a planner library database and a back-end synch module; the mobile subsystem comprising a mobile device and a mobile application; the mobile application comprising a browser application, a user interface, a mobile database, and a front-end synch module; the user profile database having a mobile program resource entity; the planner library database having a planner program resource entity corresponding to the mobile program resource entity; the mobile application configured to update the mobile program resource entity to an updated mobile program resource entity based on a user interaction with the mobile application; the front-end synch module configured to be in intermittent communication with the back-end synch module; whereby when the front-end synch module is not in communication with the back-end synch module, the mobile application is configured to store the updated mobile program resource entity in the mobile database; and whereby when the front-end synch module is in communication with the back-end synch module, the mobile application is configured to perform a synch and synchronize the planner program resource entity with the updated mobile program resource entity.

In some embodiments, the mobile application further comprises: a local database configured as an in-browser database; a service worker module configured to determine whether the front-end synch module is in communication with the back-end synch module; whereby when the frontend synch module is not in communication with the back-end synch module, the service worker module is configured to store the updated mobile program resource entity in the in-browser database; and whereby when the front-end synch module is in communication with the back-end synch module, the service worker module is configured to communicate the updated mobile program resource entity with the front-end synch module to perform the synch and synchronize the planner program resource entity with the updated mobile program resource entity.

In some embodiments the user interaction comprises a login and when the front-end synch module is in communication with the back-end synch module, the front-end synch module is configured to execute the synch with the back-end synch module and synchronize the mobile program resource entity with the planner program resource entity.

In some embodiments, when the front-end synch module at a first time is not in communication with the back-end synch module and the front-end synch module at a subsequent time is in communication with the back-end synch module, the front-end synch module is configured to execute the synch with the back-end synch module and synchronize the planner program resource entity with the updated mobile program resource entity.

In some embodiments, the user interaction comprises a request to pull the mobile program resource entity and the service worker module is configured to pull the mobile program resource entity from the in-browser database.

In some embodiments, the user interaction comprises a request to pull the mobile program resource entity and when the mobile program resource entity is in the in-browser database, the service worker module is configured to pull the mobile program resource entity from the in-browser database; and when the mobile program resource entity is not in the in-browser database and the front-end synch module is in communication with the back-end synch module, the service worker module is configured to pull the planner program resource entity from the planner library database as the mobile program resource entity.

In some embodiments, the mobile application is a fitness application, the mobile program resource entity comprises a fitness plan, and the mobile device comprises a smartphone.

Other objects, features, and advantages of the techniques disclosed in this specification will become more apparent from the following detailed description of embodiments in conjunction with the accompanying drawings.

BRIEF DESCRIPTION OF THE SEVERAL VIEWS OF THE DRAWINGS

In order that the manner in which the above-recited and other advantages and features of the invention are obtained, a more particular description of the invention briefly described above will be rendered by reference to specific embodiments thereof which are illustrated in the appended drawings. Understanding that these drawings depict only typical embodiments of the invention and are not therefore to be considered to be limiting of its scope, the invention will be described and explained with additional specificity and detail through the use of the accompanying drawings in which:

FIGS. 3A-3H illustrate some of the features of the FitForce planner subsystem;

FIG. 10A shows an example of the JSON document structure for a workout plan;

FIG. 11 shows examples of MOS-Specific Physical Standards (MSPSs), and the attributes that may be linked to PT programming elements;

FIG. 12 illustrates a table of plan characteristics and attributes captured to inform recommendation models.

DETAILED DESCRIPTION OF THE INVENTION

Figure 1A:
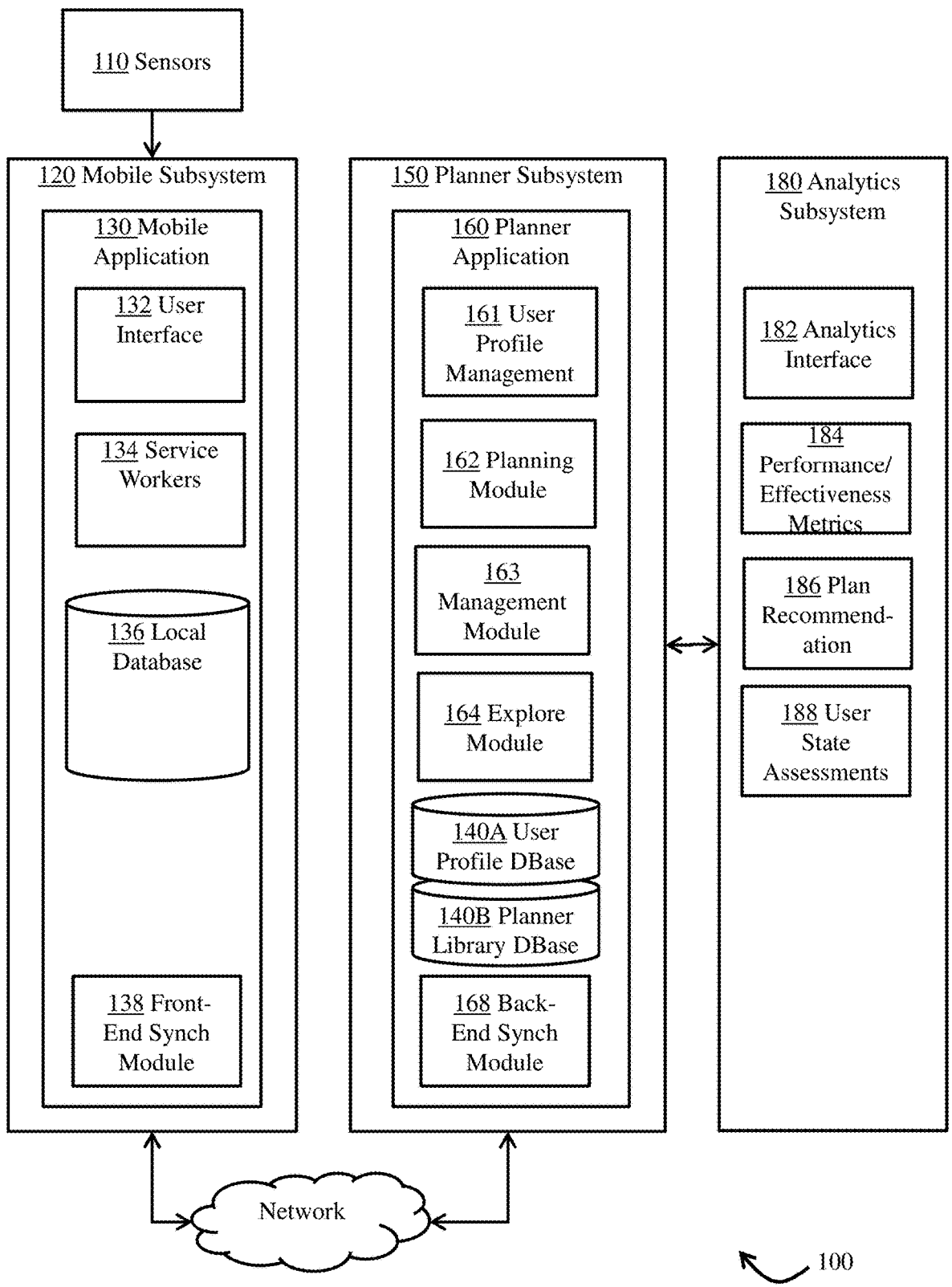
FIG. 1A shows a system diagram illustrating an example embodiment of an interactive planning system.

COPYRIGHT NOTICE: A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever. The following notice applies to any software and data as described below and in the drawings hereto: Copyright © Aptima, Inc., 2019-2020, All Rights Reserved.

Technical Problem

One objective of the interactive planner system was to provide a capability for sensing, addressing, and acting to support Navy and Marine Corps personnel physical training (PT) and readiness efforts. However, when trying to implement the system, the Force Fitness Readiness Center (FFRC) course location does not provide internet access in the classroom, weight rooms, and PT areas. This constraint forced a need for applications that can run with minimal or no connectivity yet allow FFIs to author fitness plans and submit them to course instructors for review and guidance.

Technical Solution

To address these challenges, a planner application and a mobile application were developed to support use in fully disconnected situations (offline use). The planner application is configured to support both online and offline connectivity scenarios using Progressive Web Application (PWA) technologies. This approach takes advantage of several capabilities within certain web browsers, such as:

- Local, in-browser database storage with configurable size limits;
- Service Workers as programmable in-browser network proxies that redirects application requests to locally cached/stored resources when users are offline or operating in degraded network conditions; and
- Managed temporary or persistent storage through standard browser APIs.

Coupled with the capability of Javascript functions in modern browsers, users can expect a feature set to work regardless of connectivity situation. This results in an application responsive to deployment to users in remote locations, while providing flexibility to push development updates to users when they are connected.

The interactive planner system's offline capability utilizes in-browser database storage and retrieval. In the current planning workflow, downloading resources for local use will result in the basic ability to work offline, and will also improve the user experience by minimizing the individual API requests to the online database resources.

Practical Application

The disclosed interactive planning systems and methods of use address the need for scalable tools for activities such as PT programming, execution, and analysis, within a sustainable system that can provide these capabilities available across a large organization such as a US Navy Fleet. These systems and methods provide capability for users to interactively create and manage plans in online, offline, and intermittent connectivity environments as may result from large organization working in remote and distributed areas. Providing this type of capability to remote users, with the additional capability to synchronize and centralize this type of information across a large universe of user, works around problems caused by degraded connectivity conditions throughout most of the interactions with remote users and allows for some features to operate in fully-disconnected modes.

Another example practical application of the solution for the US military is to improve combat readiness for military units. Combat readiness and addressing the training injury challenges is a driving force behind the effort because millions of US military duty days are being lost to preventable injuries and discharges. General recommendations for interventions have been made, but no technology has been developed to evaluate and communicate these in real time, or tailor them for specific situations and users. The disclosed interactive planning systems and methods fill this void and address these challenges.

Another example of a practical application of this solution is to provide performance monitoring across multiple levels of a physical training hierarchy. For example, the FitForce planning system can draw from existing military training sources to structure and augment this with training progress reports and statistics with contextual knowledge, allowing for risk assessment and mitigation recommendations tailored for maximum impact. Further, as capabilities for wearable physiological sensor technology and modeling/simulation mature and are accredited for use within the DoD, the FitForce planning system integrates and aggregates their granular event data to add to the full risk assessment picture. The resulting FitForce planning system suite of tools provides significant standalone capability to directly support PT initiatives. As a result, the military chain of command may see a fuller contextual picture of how PT impacts overall performance during a Service Member's time in the US military.

Interactive Planning Systems Overview

The disclosed interactive planning systems take advantage of broader trends toward device and operating system agnostic, mobile first capabilities that leverage services and offline data storage features within mobile and desktop browsers to deliver app-like experiences without requiring installation. Some of these capabilities, in particular Progressive Web Apps (PWAs), utilize a set of underlying principles such as reliability in uncertain network conditions, responsive user interactions and animations, and an immersive user experience where users will likely not realize the difference between the web application and a native version.

One particular embodiment of an interactive planning system, the FitForce planning system, was built to leverage these capabilities. The FitForce planning system focuses on supporting Marines and Infantry personnel with sound tools and practices that can improve the effectiveness of PT planning, execution, and analysis. FitForce planning system components—Planner, Mobile, and Analytics—will support long-term objectives of PT programming and delivery to Marines across the Fleet. The system is configured to track execution of fitness program at the unit or individual levels and the system can scale across a large number of users. Additionally, with the mobile fitness application, users can view and execute workout plans and submit these to a central repository for aggregation and analysis.

Features of some embodiments of the FitForce planning system include the following:

- Tools for PT planning, execution, and analysis of workflows and outcomes;
- Leverage wearable technologies and backend sensor aggregation datastores, and integrating these capabilities for tracking and evaluating user state at various points during PT activities;
- Providing an analytics framework that will support individual- and group-level recommendations for PT activities and plans;
- Fostering knowledge sharing through collaborative tools that connect individual users to Force Fitness Instructors (FFIs), Athletic Trainers (ATs), and Strength and Conditioning Coaches (SCCs);

Providing robust and reliable access to large numbers of users through scalable application and architecture design and deployment;

Demonstrating fitness for purpose through developmental and operational test events with end users; and Generating the content aggregation capability that will illuminate links between PT activities and outcomes, such as musculoskeletal injury (MSK-I) reduction and individual/unit readiness.

One Example Embodiment of an Interactive Planning System

As shown in FIG. 1A, one example embodiment of a network based interactive planning system 100 comprises a planner subsystem 150, a mobile subsystem 120 and an analytics subsystem 180. The planner subsystem 150 generally provides the system components that provide the planning functions. The mobile subsystem 120 generally provides remote access to the planner subsystem 150 and also provides a subset of planner functions remotely, even if not in immediate communication with the planner subsystem. The mobile subsystem 120 may take some input data from sensors 110.

Figure 1B:
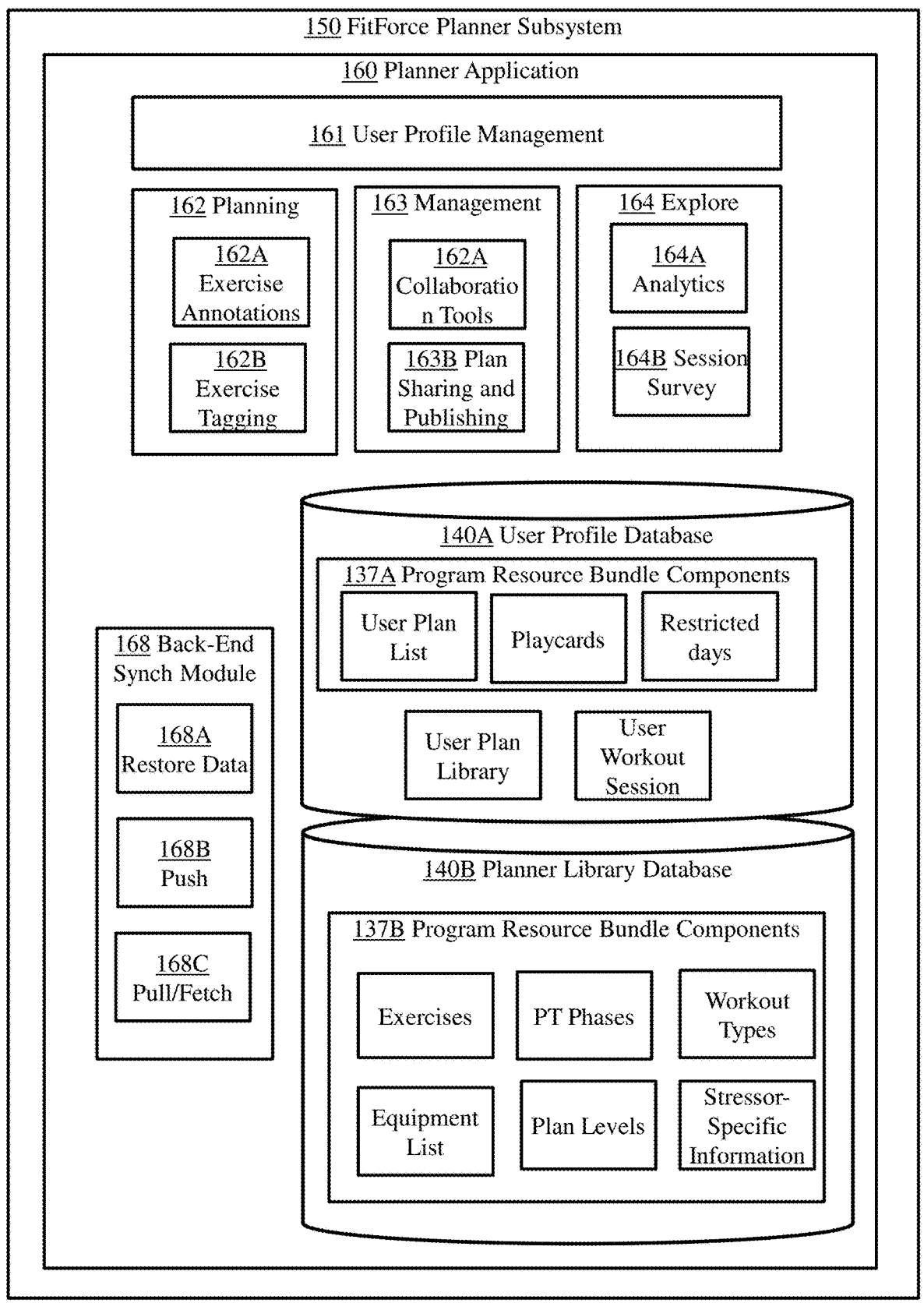
FIG. 1B shows a system diagram illustrating an example embodiment of an interactive planner subsystem.
Figure 1C:
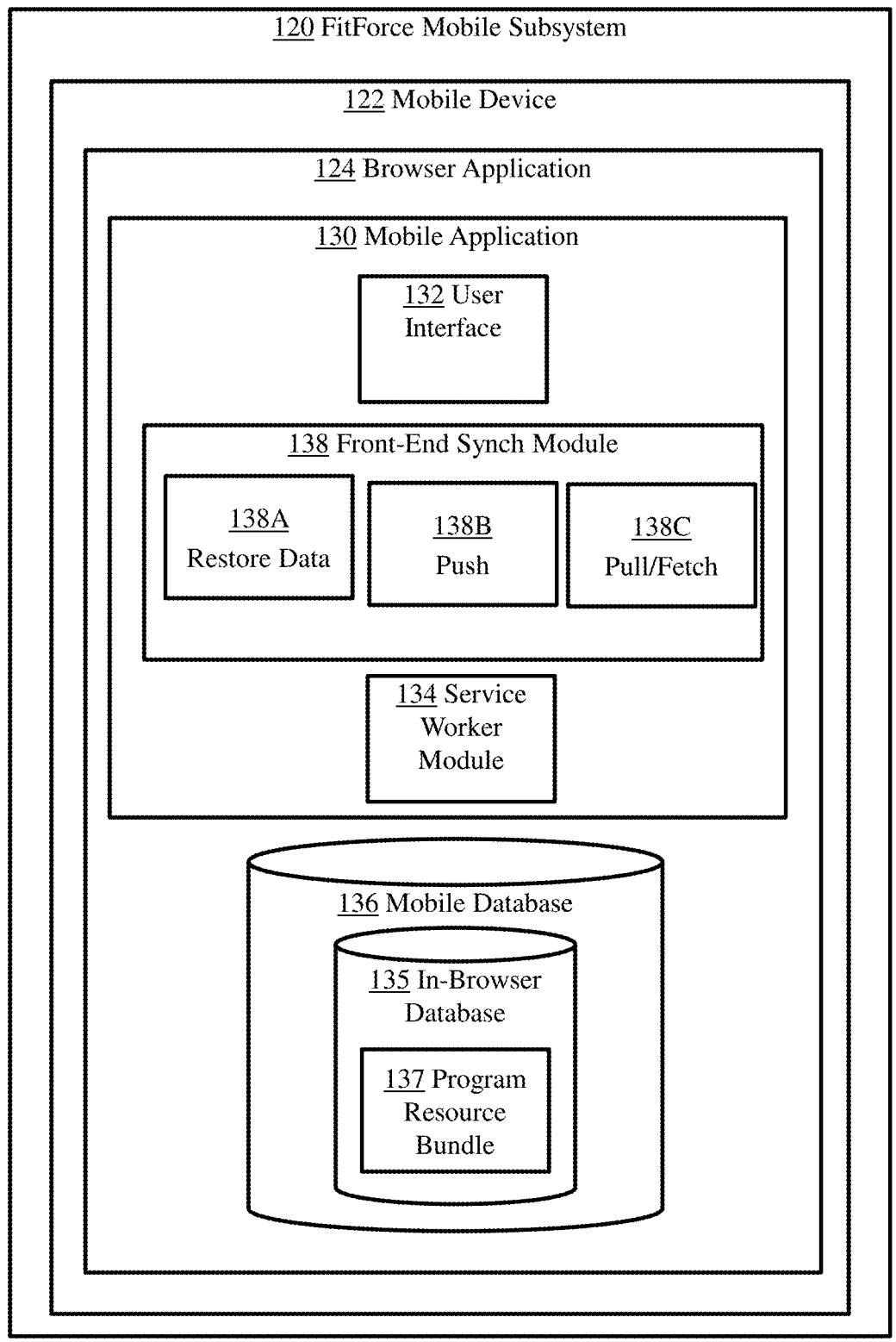
FIG. 1C shows a system diagram illustrating an example embodiment of a mobile subsystem.
Figure 1D:
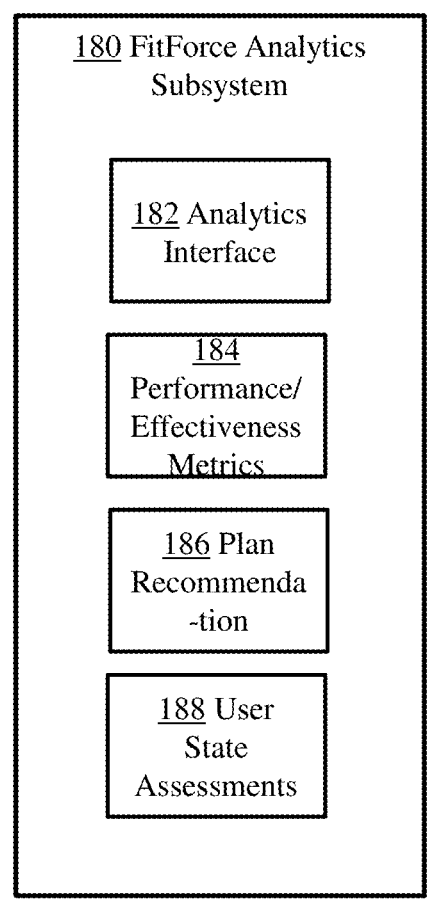
FIG. 1D shows a system diagram illustrating an example embodiment of an analytics subsystem.

One illustrative embodiment of an interactive planning system is directed to planning for physical fitness training for an organization such as the U.S. Marines. As illustrated in FIGS. 1B-1D, this FitForce planning system comprises a FitForce planner subsystem, a FitForce mobile subsystem and a FitForce analytics subsystem. In this embodiment, the FitForce planner subsystem generally provides the system components that provide the planning functions. The FitForce mobile subsystem generally provides remote access to the FitForce planner subsystem and provides a subset of FitForce planner functions remotely, even if not in immediate communication with the FitForce planner subsystem. The FitForce analytics subsystem generally provides features to analyze data generated by the FitForce planning system.

The Planner Subsystem

One example embodiment of a planner subsystem, the FitForce planner subsystem, generally provides the planning function for the FitForce planning system. In one example embodiment, the FitForce planner subsystem generally comprises a server-side application with the following features:

Provide capability for Marine users to create and manage plans in online, offline, and intermittent connectivity environments;

Provide FFIs the ability to enter in plan attributes, detail focus areas and timeframe for plan;

Provide FFIs the ability to highlight macro-level phases to inform plan analytics;

Provide FFIs the ability to create daily plans based on the playcards concept, with specified focus areas and tier structures, including detailing the number of sets, reps, and notes about the exercises; exercises should be constrained based on tier and focus area;

Provide ability to share programs to groups; and

Provide ability to create custom playcards.

Referring to FIG. 1B, the FitForce planner subsystem 150 comprises components such as a planner application module 160, a back-end synch module 168, a user profile database 140A and a planner library database 140B.

The planner application module 160 comprises a user profile management module 161, a planning module 162, a management module 163, and an explore module 164.

The user profile management module 161 is configured to generally allow the user to create and modify their user profile stored in the user profile database 140A. The user profile management module 161 will also allow an administrator to create and modify the user profile.

The user profile database 140A generally comprises the database elements particular to that user profile. In this embodiment, the user profile database 140A generally comprises information related to the user including a user plan list, playcards, restricted days, a user plan library and user workout sessions.

The planning module 162 is configured to generally allow the user to select and plan their PT activities from the planner library database 140B.

The management module 163 is configured to generally allow the user to share information with collaboration tools module 162A and publish plan information with plan sharing and publishing module 163B.

The explore module 164 is configured to generally allow the user to perform analytics on data with an analytics module 164A and perform surveys with the session survey module 164B in the planner subsystem 150.

The planner library database 140B generally comprises the database elements, or entities, that apply across the system. Entities, or planner program resource entities, are planner subsystem data structures that contain information the planner system displays back to the user. Plans, Days, and Exercises are examples of an entity. In this example embodiment, the planner library database 140B generally comprises data structures representing PT information such as but not limited to exercises, PT phases, workout types, PT equipment listings, plan levels, stressor-specific tiers, stressor-specific properties and DVIDS videos.

In one embodiment, the FitForce planner library database 140B is designed with a document store backend, where plans are created and stored as JSON files within PostgreSQL. In particular, the database utilizes the JSON Patch (http://jsonpatch.com/) schema to reduce the size of API requests and payloads. This approach offers both the required flexibility for copying and versioning plans, while also offering opportunities for synchronization performance improvements.

The back-end synch module 168 generally comprises components that allow synchronization with the FitForce mobile subsystem. The back-end synch module 168 generally allows the FitForce planner subsystem 150 to synchronize data with the FitForce mobile subsystem. This synchronization shares FitForce planner subsystem 150 information that is needed to allow the FitForce mobile subsystem operate and shares updates that may be made through the FitForce mobile subsystem.

In some embodiments, to accommodate intermittent communication or connectivity between the mobile subsystem and the planner subsystem, this synchronization is done through the synchronization of a subset of FitForce planner subsystem 150 information that is needed to allow the FitForce mobile subsystem operate if not in communication with the FitForce planner subsystem 150.

In one example embodiment, this subset of FitForce planner subsystem 150 information comprises a program resource bundle that includes components from the planner library database 140B and components from the user profile database 140A. For example, planner subsystem elements that comprise the program resource bundle components 137B may comprise:

- A complete list of available FFRC-defined exercises (n=555);
- The available PT programming phases (e.g. Hypertrophy, Power) and employment logic;
- The available workout types ("Main Stressors" such as Lower Body, Upper Body Endurance, etc.);
- Stressor-specific tiers and properties;
- Plan levels (Beginner, Intermediate, Advanced); and
- The equipment list used for selection during program design.

and user profile elements that comprise the program resource bundle components 137A may comprise:

- The labels for restricted days (e.g. "Weekend", "Holiday", etc.);
- Individual daily activities ("playcards"); and
- The user's plan list.

The images in FIG. 3A-3H illustrate some of the features of the FitForce planner subsystem including the following:

- Program creation, including macro/meso/microscale phase specification;
- Creation and editing of individual daily activities ("playcards") using a set of standardized focus areas, exercises, training blocks ("Tiers"), and FFRC guidance for sets/reps/loads by phase;
- Generation of custom playcard types;
- Visualizations showing the balance of a program by playcard type;
- One-click playcard printing;
- Capabilities for publishing these plans to groups;
- Group creation, invitation, and management capabilities;
- Maintenance of a plan library at the individual user level;
- Group-based analytics, including attendance and workout survey aggregated statistics; and
- Basic user account management.

The Mobile Subsystem

The mobile subsystem generally comprises the client-side components for the interactive planning system.

Referring to FIG. 1C, in one example embodiment, the FitForce mobile subsystem 120 comprises a mobile device 122 and a browser application 124 that includes a mobile application 130 and a mobile database 136. In this embodiment, the mobile application 130 is a progressive web application comprising a user interface 132, service worker modules 134, and a front-end synch module 138. The mobile database 136 generally includes the entities, such as program resource entity 137 data, that are stored locally with that mobile device 122. In some embodiments, the mobile database 136 comprises an in-browser database 135. The mobile application 130 operates within the browser application 124 and utilizes the browser database functionality and browser APIs.

The mobile application 130 is downloaded by a user's browser from the planner subsystem server. The mobile application 130 is executed on the user's browser 124 and communicates with the planner subsystem databases during synchronization. As a progressive web application, the mobile application 130 loads a minimal user interface 132 as soon as possible and then caching it so it is available offline for subsequent visits before then loading all the contents of the app. When the user visits the mobile application 130 from the device 122, the user interface 132 loads from the cache and any new content is requested from the server (if it isn't available in the cache already).

The mobile database 136 comprises a local database of entities, also called mobile program resource entities, that are used by the mobile subsystem 120. In this embodiment, these entities may be stored consistent with the browser and browser APIs such as the Mozilla IndexedDB API. As an example, IndexedDB is a client-side storage capability in most browsers (e.g., Mozilla Developer Network (MDN) API Documentation) that the mobile application utilizes for storage of entities offline. IndexedDB lets you store and retrieve objects that are indexed with a "key." All changes that you make to the database happen within transactions. IndexedDB is an asynchronous API that can be used in most contexts, including service workers. Service workers 134 are a means for web content to run scripts in background threads. The worker thread can perform tasks without interfering with the user interface. Once created, a service worker 134 can send messages to the code that created it by posting messages to an event handler specified by that code (and vice versa). IndexedDB can be used to store more than just simple text strings. It also supports the storage of complex objects such as video or image blobs.

The front-end/mobile and back-end/planner databases share a document data model for optimization purposes.

The front-end synch module 138 is configured to synchronize the mobile database 136 with information from the FitForce planner subsystem. This synchronization updates program resources entities, mobile program resource entities and planner program resource entities, through synch actions performed by the front-end synch module such as:

- Restore Data 138A—Updates an in-memory collection of entities with data from IndexedDB, which refreshes the data displayed in the mobile application;
- Push 138B—POSTs any pending API requests, such as updated entities, to the back-end with data from IndexedDB. Entities are marked with a flag that the application translates into an API request to be executed; and
- Pull/Fetch 138C—GETs entities, such as updated entities, from the back-end planner subsystem and stores them in the browser's IndexedDB.

Entities have a property that defines the amount of time they are cached in the client's browser until they are pulled again. Volatile entities have a shorter duration, while stable entities are cached longer.

Service workers 134 essentially act as proxy servers that sit between the mobile application 130, the browser 124, and the network (when available). They enable the creation of effective offline experiences, intercept network requests and take appropriate action based on whether the network is available, and update assets residing on the server. Service workers 134 will also allow access to push notifications and background synch APIs.

Figure 4A:
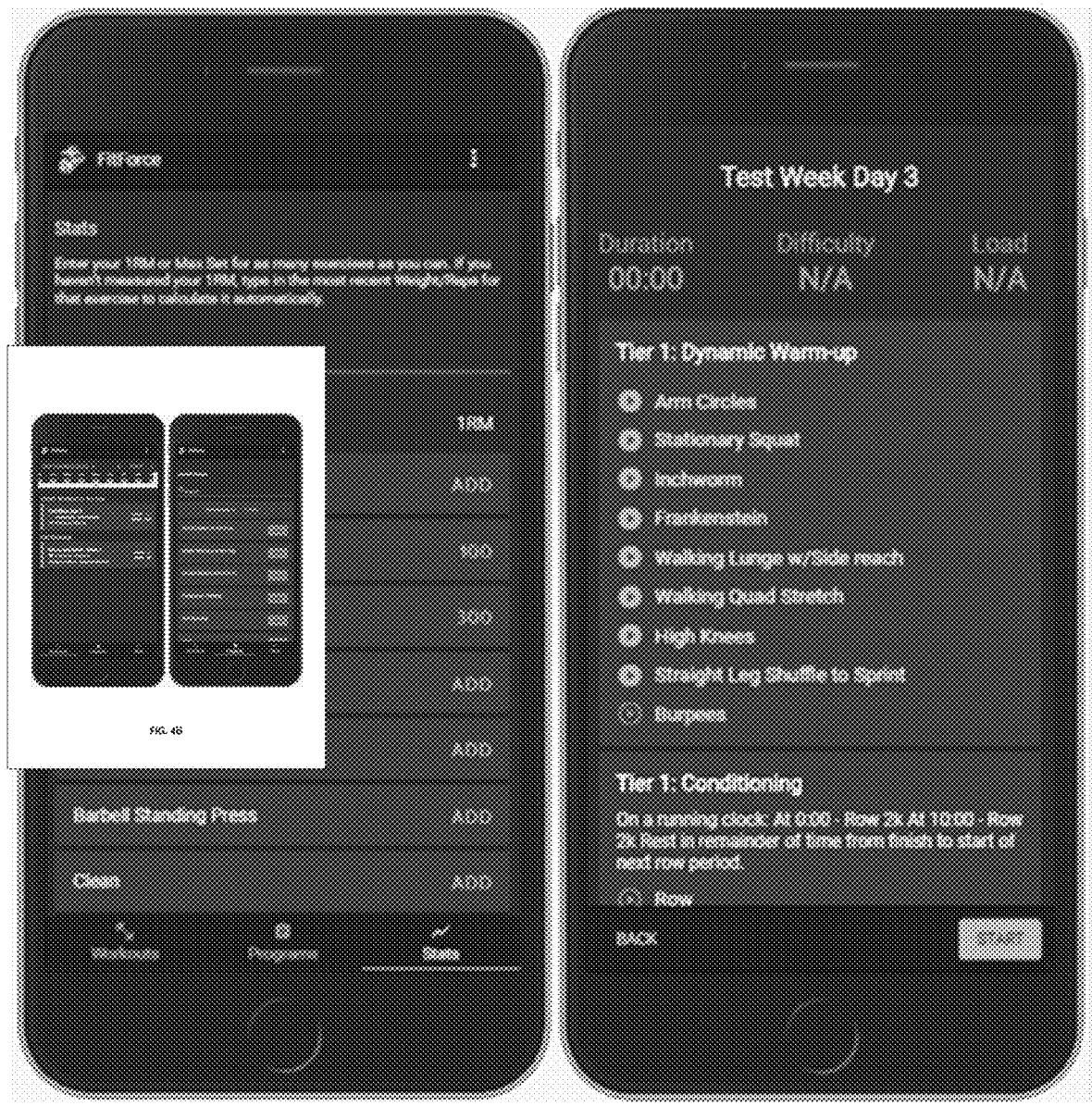
FIGS. 4A and 4B show example embodiments of a user interface to the FitForce mobile application allowing a user to view and execute the PR programs assigned to their groups.
Figure 4B:
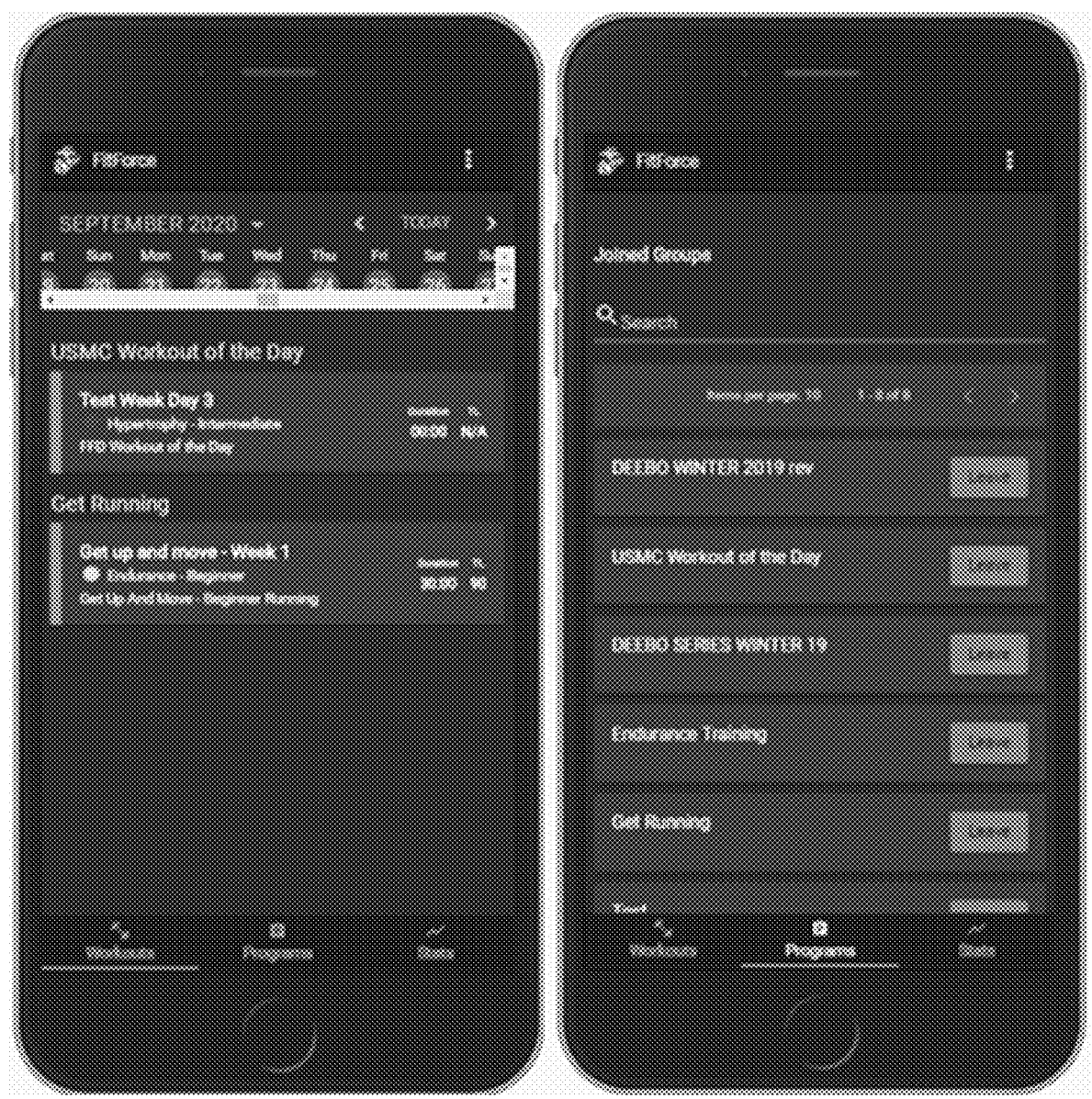

FIGS. 4A and 4B show example embodiments of a user interface to the FitForce mobile application, which allows users to view and execute the physical training plans assigned to their groups. Example features of the mobile application include the following:

- Ability to select groups and programs assigned to those groups;
- Display of the playcards that comprise a program;
- Ability to run through the playcards as an individual or as a group PT leader; the latter allows the PT leader to specify who from the group attended the workout session, so those individuals will not need to complete the session in their own accounts;

A user interface where users can view and check off completion of individual exercises and tiers;

Links to streaming DVIDS videos showing the proper technique for individual exercises, generated by the FFD;

Workout session syncing with the FitForce backend; and

Optional ability to deploy a workout session survey to participants where they can provide feedback on the difficulty of the session, as well as other attributes related to sleep, nutrition, and general wellness on the day of the activity.

Many of the above features, including the full playcard completion workflow, is supported in a fully-offline connectivity mode. By making these features available offline, more users can be supported in typical fitness scenarios and locations where there may be poor connectivity.

The FitForce planner system's offline capability may utilize in-browser database storage and retrieval whereby downloading resources for local use will result in the ability to work offline and will also improve the user experience by minimizing the individual API requests to the online database resources.

The FitForce mobile subsystem user interface supports many of the touch interactions users have come to expect, such as swipes, holds, and between-screen transition patterns. Additional features may include the following:

Reorganization of the mobile app to provide full playcard previews, where users can interactively look through future playcard exercises and videos before starting the exercise session;

Specification of app behavior through a custom web app manifest, where we can designate a home screen icon, how the app opens in various mobile browsers (e.g., full screen), default orientation, scope, and any required splash screens;

Design and development of a workflow for guided exercises, where individuals and groups can execute circuit training guided by timers and exercise notes;

Support of alternative exercise description media, such as GIFs, pictures, and text; and Routes to individual/group statistics on the mobile interface.

With experience having severely degraded connectivity conditions throughout many embodiments of the planning system, it becomes important for some features to operate in fully-disconnected modes. Fortunately, mobile browsers available on both iOS and Android support the underlying technologies that enable PWAs to operate in this mode, provided the application has been designed and optimized to check for the state of connectivity and adapt accordingly. The FitForce mobile application supports fully-offline execution of playcards, so users are able to conduct activities such as group-led PT in areas with poor/no cell phone reception or wifi. It is also beneficial for other components such as the FitForce planner application to be able to operate in very degraded conditions.

The FitForce Analytics Subsystem

Referring to FIG. 1D, the FitForce analytics subsystem 180 allows systems users to understand how units and individuals were executing the programs generated using the FitForce planner application, and how to best convey this information through intuitive visualizations and aggregations. The FitForce analytics subsystem 180 may provide group-level aggregations of playcard attendance and survey results. The FitForce analytics subsystem 180 may be accessed with an analytics interface 182 and may perform activities with performance/effectiveness metrics module 184, a plan recommendation module 186 and a user state assessment module 188.

Figure 5A:
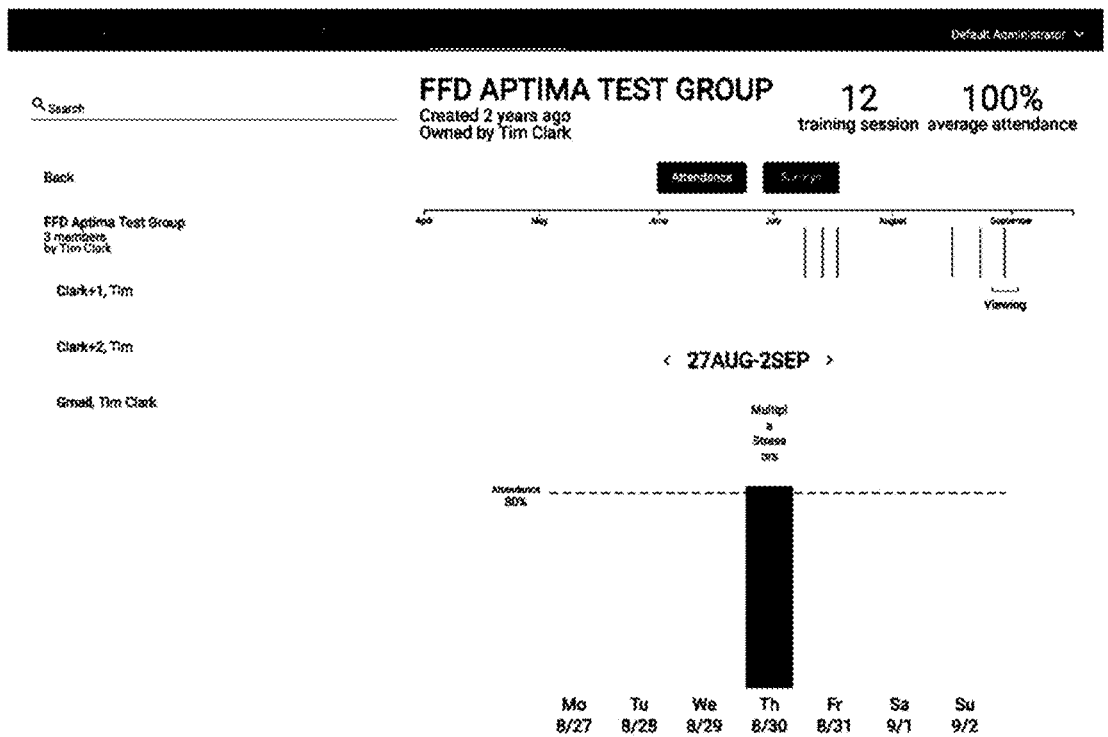
FIG. 5A illustrates an example FitForce Analytics interface showing group-level aggregations of attendance by playcard type and date.
Figure 5B:
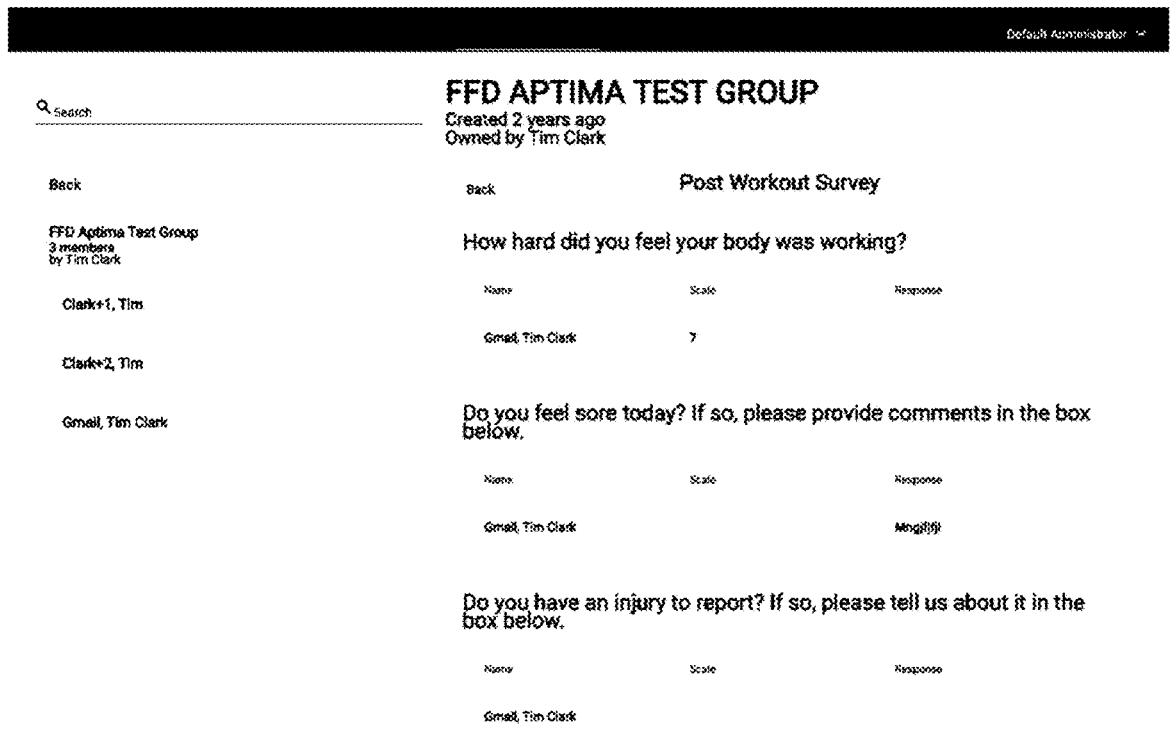
FIG. 5B illustrates an example FitForce Analytics interface showing workout session survey responses by group members.

The images in FIGS. 5A and 5B show visualizations and rollups of group activity. FIG. 5A shows an example FitForce Analytics interface, showing group-level aggregations of attendance by playcard type and date. FIG. 5B shows and example workout session survey responses by group members. This capability can be integrated with other survey results, e.g., those expected from Smartabase daily subjective questionnaires delivered to SOI-E Marines.

The FitForce analytics subsystem 180 uses an analytics data model to support efficient front-end access to relevant data aggregations and information constructs. This data model has been designed to enable faceted search through a flexible user interface. Users at multiple levels will be able to drill down and aggregate on features of PT programming relevant to the questions they are trying to answer. For example, a TECOM stakeholder can initiate a faceted search to answer questions about the average amount of time it takes to complete Lower Body Endurance playcards by various units and determine injuries occurring during training over time.

The analytics data model may also enable interaction with system data and information from both the FitForce planner application and FitForce mobile application to enable the following:

Support for ad hoc queries in the FitForce planner application interface using flexible frontend components such as cascading drop-down option lists and filter/faceting checkboxes;

Support for aggregations of individual performance data on the Mobile interface; and Tuning the data model to support any required performance specifications and user experience optimizations.

One result of the FitForce planner application is to sufficiently identify and emphasize the links between the programs (or plans) and their intended effects. Following a "do-no-harm" approach, this helps ensure that users are not overtraining and subjecting themselves to higher risk of injury. Another approach is to focus on performance optimization, where users will benefit from plans designed to increase strength, flexibility, and lethality across a group of users.

As an example of how goal-oriented programs can be used, consider the Physical Fitness Test (PFT). A generic program can be developed to guide individuals on their path to the desired rating, be it First Class or simply an improved score. However, Marines in the program may face perturbations such as soreness and pre-injury conditions that shift the focus of the program to injury prevention, perhaps at the cost of reaching their desired rating. This balance between goals and injury prevention can dramatically influence the recommended adaptations, particularly when individual histories are concerned (e.g., a Marine with a significant history of knee injuries has a different level of susceptibility to injury than another with a different history).

As another example of how goal-oriented programs can be used, the Fit Force planner system can be used to understand the variations in approaches required for a traditional measure of fitness, such as the PFT, versus more nuanced fitness requirements, such as for individual Military Occupational Specialties (MOSs) or operational focuses (see FIG. 11). The PFT is an example of aligning with developed program training goals, where score-based assessments based on core exercise demonstration are highly structured and standardized to create a metric generalizable across MOSs. However, the FitForce planner system may also support programs designed to improve performance and readiness for MOS-Specific Physical Standards (MSPSs), which may vary in terms of the muscle groups, foundational movements, and tasks required to effectively do the job.

The FitForce planner system leverages the knowledge and skills of Marine Corps SMEs as they generate their own programs for specific goals—traditional (like for PFTs) or more nuanced (like MOS standards). Specific program characteristics can be learned (e.g., periodically repeating pull-up series, emphasis on core strength, focus on the press foundational movement) that may be important components for achieving the programs' stated objectives. This helps evaluate the muscle groups and capabilities required to perform MOS-specific tasks. The FitForce planner system may also leverage data from both the PT leaders as they monitor individual Marines and make programmatic changes and the progress of Marines undergoing these goal-focused programs. With the appropriate IRB approvals in place, analyses of these data may help identify (1) appropriate types of program changes for the purpose of either injury mitigation or performance optimization and (2) the extent to which specific programs—or program characteristics—are successful in growing Marines toward a target physical fitness objective.

Plan Recommendation Algorithm Development. A feature of the FitForce application includes a library of vetted fitness plans accessible to all Marines. Through this interface, Marines are empowered to reach their physical fitness goals by engaging in a safe and effective plan of their choosing. Initially, plans will be created only by knowledgeable professionals (e.g., ATs, rehabilitation/injury prevention experts, SCCs) and trained FFIs. This limits offerings to those plans that have a higher likelihood of minimizing risk of training-related injuries. Depending on the Marine's desired fitness outcomes (e.g., a First Class score on the Physical Fitness Test [PFT]), the library of available plans will downselect to recommend only those that are capable of progressing the Marine through a series of PT sessions meant to meet his/her specified goal(s). Furthermore, Marines will have the option to additionally filter offerings according to other limitations or characteristics (e.g., 2 months long, sessions 5 days/week, no equipment required).

FIG. 12 illustrates describes many of the plan characteristics; they range from usage statistics to descriptors of effectiveness to useful logistical qualities important for plan execution. A number of these characteristics are specified by plan authors (e.g., descriptions, goal, training level, injury recommendation) during the process of uploading a plan to the library. One subset of characteristics are automatically populated based on plan attributes tagged in the underlying data model (e.g., duration, days/week, resources needed, group/individual recommendation).

The remaining characteristics may be populated after the plan is executed by trainees. FitForce applications will securely track which users undertake which plans (and to what extent), thereby enabling Marines to provide ratings and comments about their experiences with specific plans. Lastly, through these same user-tracking mechanisms, when users enter in voluntary demographic information (e.g., PFT score, weight) at the start and conclusion of a plan, the application will be able to determine—on average—the potential impact that a plan has on weight or PFT Score, or realistically, any value worth tracking. Again, these trend analyses relating plans to outcomes are especially valuable for the future of the Marine Corps, and even beyond for the other services interested in evidence-based PT.

Injury Forecasting. Algorithms may also be used for monitoring individuals in terms of their risk for injury. The output from these injury likelihood algorithms may contribute to the future automated plan modifications that make individualized PT more attainable for the Marine Corps. Marine trainee state may be monitored in a manner that is supported by the scientific literature—Training Stress Balance (TSB; Hulin et al., 2014; Gabbett et al., 2016; Cross et al., 2015).

The algorithm for calculating TSB from FitForce Planner programs may follow these steps:
  For each workout session, calculate a measure of external workload—something related to how hard the body physically worked (e.g., load, volume, intensity);
  For each workout session, calculate a measure of internal workload—something related to how the workout felt (e.g., rating of perceived exertion [Foster et al., 2001]× session duration);
  Separately for external workload and internal workload, average the past week's worth of workload values; this is the acute workload;
  Separately for external workload and internal workload, average the past month's worth of workload values; this is the chronic workload; and
  The size of the acute workload in relation to the chronic workload computes to either a negative or a positive TSB.

A neutral or close-to-neutral TSB indicates a balanced loading, i.e., the trainee is neither over—nor under-trained, and therefore currently in a good readiness state to undertake a workout session. A balance that is too extreme at either end suggests that care should be taken when deciding what to include in the trainee's next workout or whether to skip the workout altogether.

Workload values may be obtained from both survey and sensor inputs to calculate these workload values. Additionally, subjective self-report metrics can be collected with the FitForce mobile subsystem alongside objective inputs about plan completion.

Other FitForce Planner Features

Plan Sharing and Publishing. A plan sharing and publishing module provides the ability to share a program/plan across units and individuals. Features for plan sharing include the ability to collaboratively develop a plan across multiple users and deliver these plans to groups to which the plan is shared. Features for plan sharing may also provide for plan templating, publishing, and sharing of not only full programs, but also of relevant independent components (e.g., phases, individual playcards, and tiers [blocks]). This enables a more sustainable plan creation and sharing ecosystem, where FFIs, ATs, and SCCs can produce widely-applicable template plans for units or individuals to instantiate within their own unique operational environments. For example, a general-purpose 16-week Personal Fitness Test (PFT) improvement program may be shared. These programs have been designed by expert athletic trainers and strength and conditioning coaches, and are meant to support a wide range of individual skill levels. This sharing may also (1) provide access to these programs within the scalable FitForce planner application and FitForce mobile application interfaces; (2) allow them to be adopted and adapted by FFIs assigned to units to tailor to their unique operational needs (e.g., change dates for playcards, add challenge days, fit around existing POIs for schoolhouses); and (3) track not only how these plans are being executed, but if/how they are being adapted to operational realities in different geographic regions, units, and operational tempo conditions.

Figure 6A:
FIG. 6A illustrates one example embodiment of the FitForce planner library landing page.
Figure 6B:
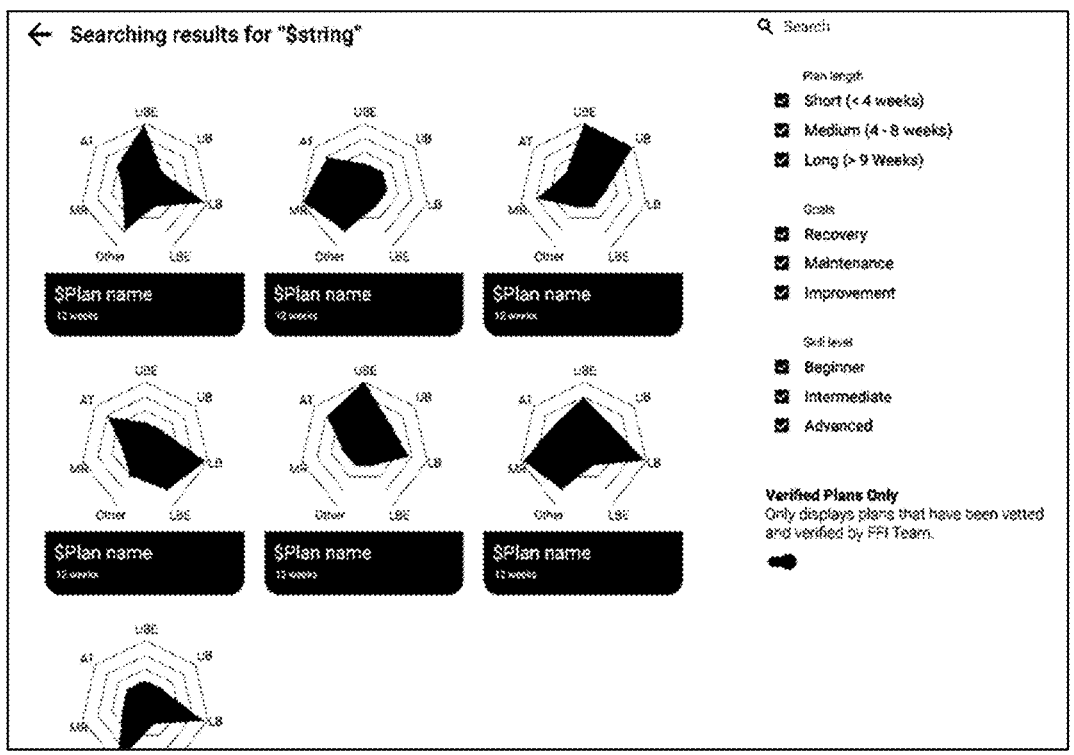
FIG. 6B illustrates one example embodiment of a planner library selection process.
Figure 6C:
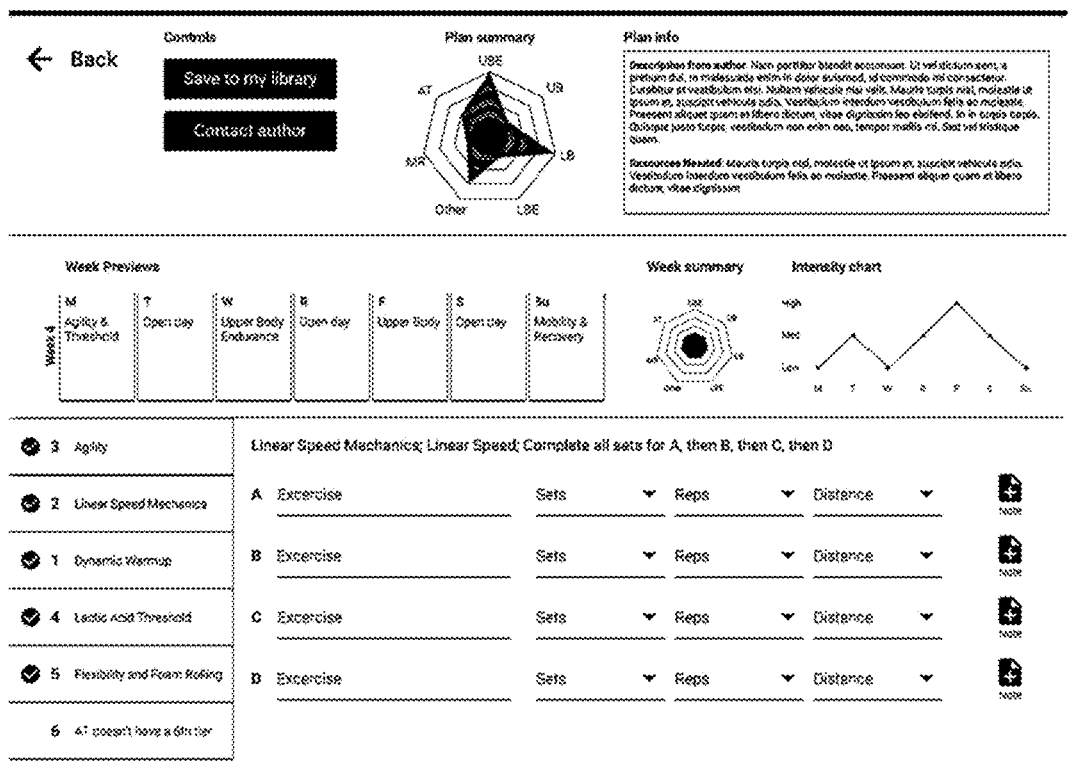
FIG. 6C illustrates one example embodiment of an instantiation of a plan from the planner library.

FIGS. 6A-6C illustrate one example embodiment of the FitForce planner library, where users can search for plans, evaluate a plan, add the plan to their own libraries, and create instances of the plans for execution.

FIG. 6A illustrates one example embodiment of the FitForce planner library landing page mockup. This provides a starting point for users at various levels (e.g., individual Marines, FFIs, unit leaders, etc.) to browse and search for plans based on attributes relevant to their specific operational needs.

FIG. 6B illustrates one example embodiment of a planner library selection process. This interface shows the ability to filter on attributes related to duration of the program, any specified goals, required skill levels, etc. Plans can be represented in an intuitive "card" format, where visualizations on factors such as plan balance by stressor provide users with more detailed information of the playcards that comprise the program.

FIG. 6C illustrates one example embodiment of an instantiation of a plan from the planner library. In this interface, users can choose to add the plan to their own library, thereby creating an instance of the plan that can be edited as necessary. This would all be done from a unified workflow, minimizing the steps to progress from plan search to implementation.

One enabling component to support the desired user adoption and subsequent generation, aggregation, and analysis of content are collaboration tools that can (1) connect Marines with expert-curated physical fitness training programs based on their personal attributes and interests, (2) foster communication between and among key stakeholders to propagate expert knowledge from the sports-medicine and exercise science domains, and (3) provide the ability for Marines and others involved in the plan creation and execution to provide qualitative and quantitative feedback on the physical fitness programs and plans. Supporting communication among FFIs, ATs, and SCCs, as well as the Marines they are responsible enable the sharing of information at scale, while providing tools that can identify the risk of injury and provide methods to improve communication in generating plan mitigations to maximize performance.

The FitForce planner subsystem may also support a Marine-driven method of connecting with FFIs and other fitness experts available to the Fleet. For example, perhaps a Marine hears about the FitForce system from a friend in another company. To support this, the FitForce planner subsystem may provide the ability for the Marine to be able to request an account, and find a relevant group to join based on his/her physical fitness level or particular fitness objective, without having direct access to an FFI initially. A Marine may want to start in a group aimed at improving PT scores or focusing on upper body strength based on an upcoming deployment, or working on rehabilitation after an ACL injury. Here the Marine can search for groups to join based on his/her particular situation and fitness objective. Once the Marine joins a group, this person may be connected with a fitness expert, such as an FFI, AT, or SCC to target and modify his/her plans and programs based on individual circumstances. These features include support for searching and identifying groups and PT programs from the library once a Marine has joined the application. These groups can be managed by experts, such as FFIs, ATs, or SCCs, whereby we could then prompt a Marine to "get connected" with an expert for monitoring and feedback. Within the FitForce planner application, FFIs can monitor the groups they are responsible for, as well as identify new Marines who have joined and requested to get connected to an expert.

Figure 7A:
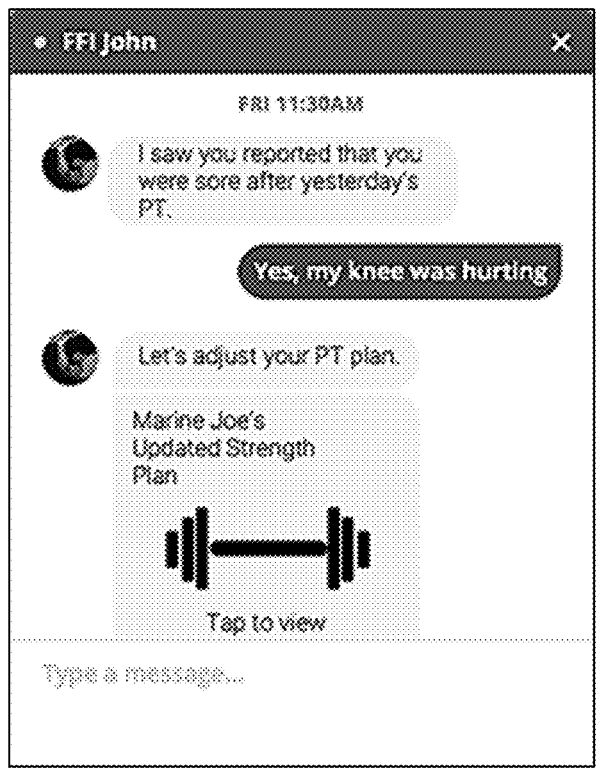
FIG. 7A illustrates an example of a chat conversation between a fitness instructor and a user in a post-workout survey.

Messaging. Once a Marine has been connected with a fitness expert, communication tools, such as in-app messaging, can support collaboration between and among the Marine and the FFIs, SCCs, and ATs, to address injury risk and plan mitigations based on program execution and feedback. For example, as the Marine is executing a particular PT program, as part of the daily post-workout survey perhaps he/she reports experiencing knee pain or soreness after a PT session. In this case, the FFI, in viewing the analysis of survey data, can see that the individual in question has reported consistent soreness in this area and may require a plan modification in order to prevent injury. The FFI, however, may be responsible for hundreds of Marines, and is unlikely to be able to meet in person with this individual. Here we intend to support the ability to send in-app chat messages between the expert and the Marine, where the expert can ask about the soreness and discuss plan modifications to focus on recovery and strengthening of the surrounding muscle groups to mitigate potential further damage. Through chat, the FFI can check in periodically to determine how the modified PT plan is going, while also monitoring plan execution and survey responses in FitForce Analytics modules. For example, FIG. 7A gives an example of a chat conversation between an FFI and a Marine regarding soreness that the Marine reported in his post-workout survey; based on the analytics from the FitForce Analytics module, perhaps this Marine is at risk for overtraining. Here the FFI can discuss modifying the PT plan and can share the plan out to the Marine for a quick review to mitigate potential injuries.

Figure 7B:
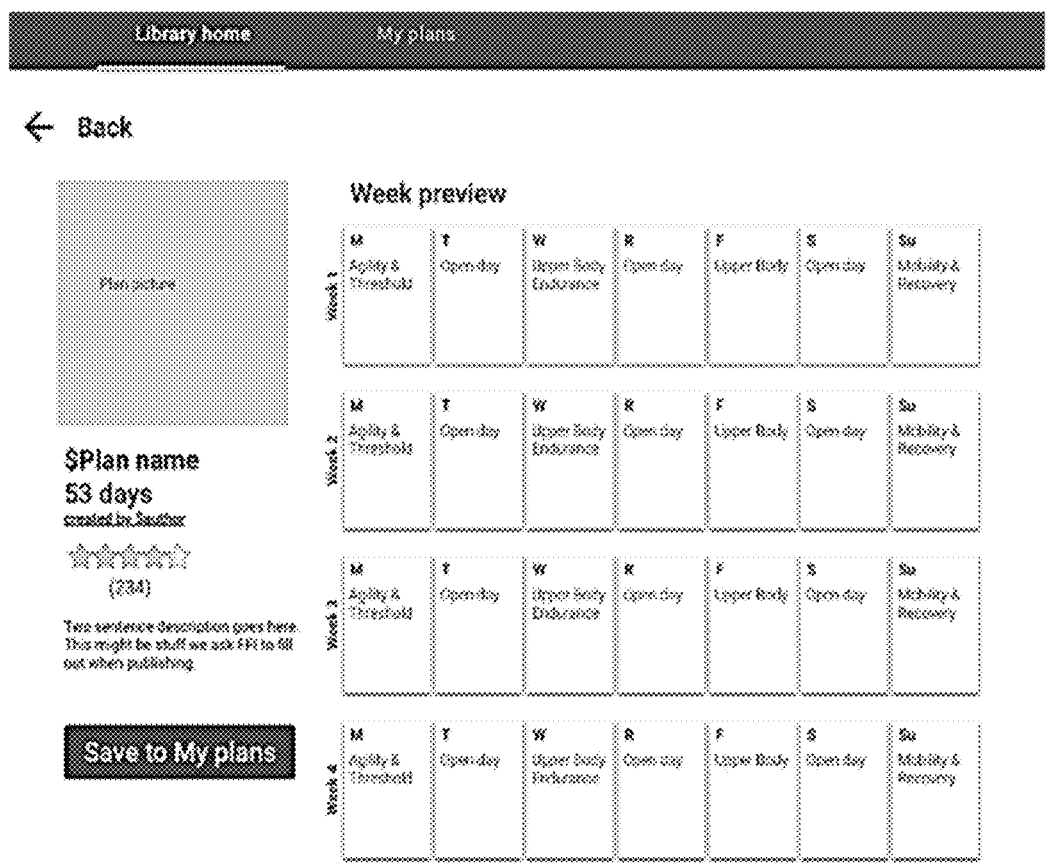
FIG. 7B illustrates an example summary of the star ratings for a sample plan.

As part of the plan-sharing infrastructure, FFIs, SCCs, and ATs may be able to review and update plans collaboratively. In this case, perhaps an FFI can have an AT review the plan, or comment on its feasibility for a certain cohort. Marines may also have ability to provide feedback on the plans and programs they are executing, such as providing ratings, which can then inform recommendations in future phases of this effort. To support this, there are front-end interfaces to support providing ratings (such as a five-star scale familiar to most users), that will feed into a back-end data model that stores this information at the plan and program level. Feedback can be analyzed to determine the most popular plans for specific objectives such as PT score improvement or rehabilitation after injuries as part of the recommendation algorithm. FIG. 7B gives an example summary of the star ratings for this sample plan.

As part of the collaboration ecosystem, the FitForce system may also provide plan effectiveness and unit- and individual-level statistics of program execution aggregations and summary reports to unit leaders and commanders. For example, a commander may want to understand the readiness level of a company prior to deployment. In this case, the FFI who has been tracking and monitoring the PT of the unit, as well as their post-workout surveys detailing injuries and other risks, can provide summary statistics detailing the readiness of the unit based on physical fitness and performance. With the addition of monitoring and tracking components, such as wearable sensors in future phases of this effort, biophysical measurements can provide more automation and more granularity to assist in providing a robust user assessment metric to inform readiness.

Exercise Annotations. In some embodiments, exercises may be annotated with contextual knowledge that will serve as a basis for providing important program analytics, as well as automating many of the mitigations, regressions, and equipment linkages within the FitForce planner, FitForce mobile, and FitForce analytics subsystems. For example, each exercise or group of exercises may be annotated with concepts such as:

Foundational movement;
Muscle group(s);
Required equipment;
Required skill level; and
Regression chains.

Figure 8:
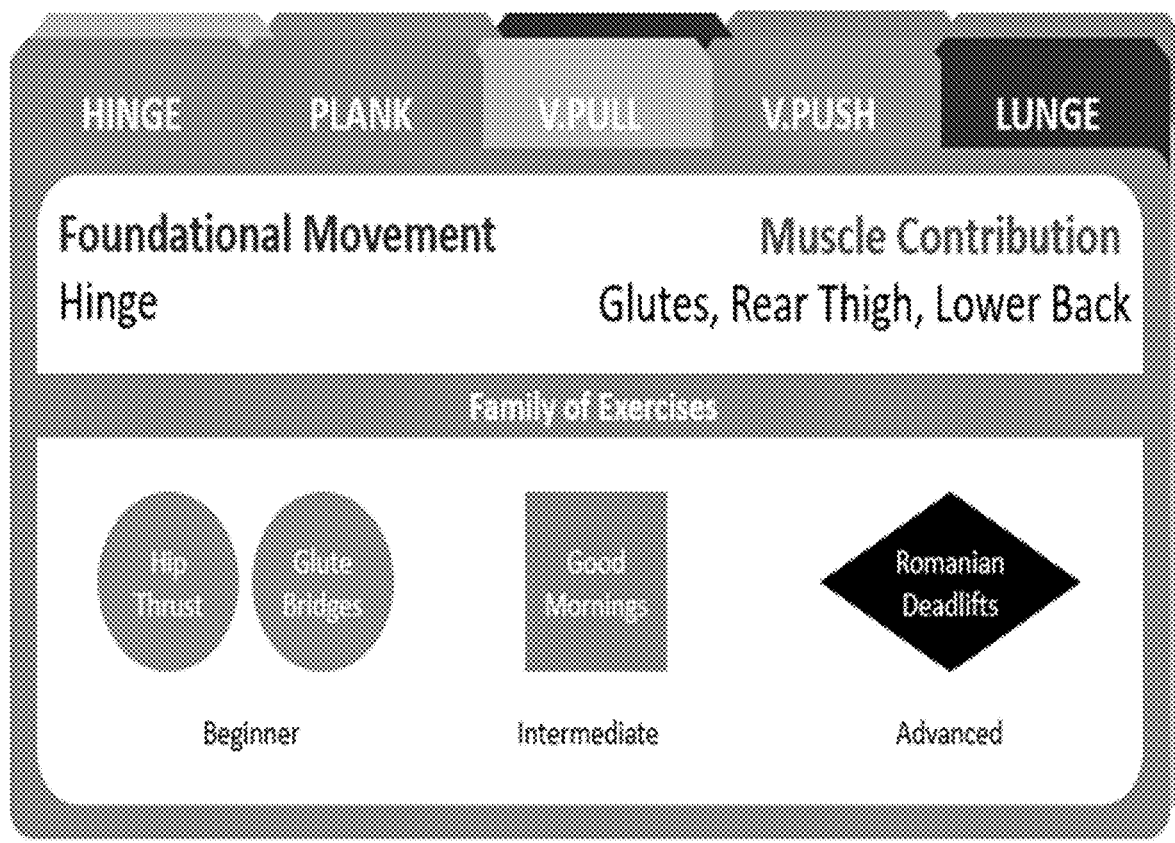
FIG. 8 illustrates an example FitForce Analytics interface showing exercise characteristics.

An example of how these areas could visually be organized in an exercise library is provided in FIG. 8 showing exercise characteristics for informed training plan decision making.

Foundational movements may be defined as the gross motion the body (or body region) undergoes to complete an exercise. Hip thrusts, for example, entail the hip joint extending and flexing—a motion important in picking up heavy objects and stabilizing the torso during movement. Hip thrusts fall within the foundational movement group of "Hinge" motions. In training approaches where operational-role or task-specific performance is of value, providing a category for foundational movement can quickly present associated movements to deliver desired functional improvements. Foundational movement annotations thereby offload the cognitive load required to recall a large number of relevant exercises. By incorporating these types of annotations when generating programs, fitness planners will be able to search and filter exercises by foundational movements, as well analyze plans to determine if the appropriate balance of foundational movements is represented by the exercises contained therein.

Next level filtering and annotating of exercises may be done through the net contribution of key muscles to each exercise. The recruitment of particular muscles not only trains the muscle, but also triggers muscle fatigue and recovery processes. Providing exercise planners with insights on which muscles are targeted in a training session improves contextual awareness and allows a direct connection between exercise groups and muscle performance to be made. In this way, muscle activity or contribution annotations not only give immediate planning guidance (i.e., overuse avoidance, muscle targeting), but also can facilitate trainer learning. We intend to build out within the planning interfaces analytical modules that will support plan and program analysis based on the determination not only of the foundational movements represented, but on a breakdown of the muscle groups as well, to enable planners to have a higher level overview of the balance between various muscle groups that are targeted in their programs.

The first two annotation types serve to provide physiological and operational-movement insights to broadly identify or filter groups of exercises. Once the trainer is informed, executing a desired workout requires specific equipment, which is best accounted for in the planning phase. Annotating the exercise planning interface with the required tools and equipment serves to facilitate resource coordination within the training environment and can lead to increased efficiencies (per unit time in the gym). In addition, access to proper training equipment (and corresponding technique awareness) prevents training injury. Here we envision that with each exercise linked to the necessary equipment to execute that exercise, a planner could quickly preview upcoming workouts to ensure that the appropriate equipment (e.g., a TRX) has been acquired or reserved.

Whereas exercise equipment is critical to conducting an exercise, the skills needed to safely exercise at a certain intensity need to be gradually developed. Because poor matching between strength requirements and individuals' strength can lead to severe injury or undertraining, it is important to provide FFIs information on the strength (or training proficiency) of an individual during exercise planning. As shown in FIG. 8, four different exercises are found within the combined category of "hinge-like foundational movements" that target the muscle activity in the "glutes, rear thigh, lower back." Segmenting of these exercises by the relative training level requirements provides FFIs insight to prevent injury, but also outlines a clear progression from exercise to exercise as the trainee becomes stronger.

Lastly, regression chain annotations include alternative exercise routines or exercise modifications to accommodate sub-optimal performance (i.e., due to injury, sickness). The availability of such information not only allows FFIs to plan effective exercise routines for injured personnel (as opposed to immobility or bed rest) and also provides accessible alternatives to address in-training injuries or pains. These annotations enable important functionality for regression and mitigation planning. If a Marine has a muscle group that is injured or at risk of injury from overtraining, then the planner can view all of the exercises in his/her program in the next week for example, that will impact that muscle group, and quickly plan regressions or modifications to prevent injury in a semi-automated fashion through the regression chain annotations.

FitForce Planner Deployment Architecture. A significant challenge during early implementations was the design, development, and deployment of a suite of web-based applications that can both scale to ~200,000 users and function seamlessly in degraded connectivity situations. In field testing and demonstrations, the FitForce planner system faced severe connectivity constraints, forcing consideration of web-based tools for these dynamic situations. The resulting design for cloud deployment of FitForce Planner may support vertical and horizontal scaling of frontend and backend components, consider tradeoffs and deployment opportunities for continuing our offline-capable Progressive Web Application (PWA) approach, and support native Android and/or iOS applications.

FitForce Planner Backend Design. Some FitForce planner system backend design embodiments may be based on a graph database. However, graph databases typically are not designed for a workload to include thousands of user. Another embodiment of the FitForce planner system backend uses a traditional relational database as its primary database, and will then synchronize its state into any analytics databases required (e.g., a graph database). Relational databases are proven and mature for this type of workload. As the system scales up to hundreds of thousands or millions of users, this architecture allows migration to big data NoSQL technologies.

To address limitations and challenges encountered to date, additional technical approaches are envisioned.

Figure 9A:
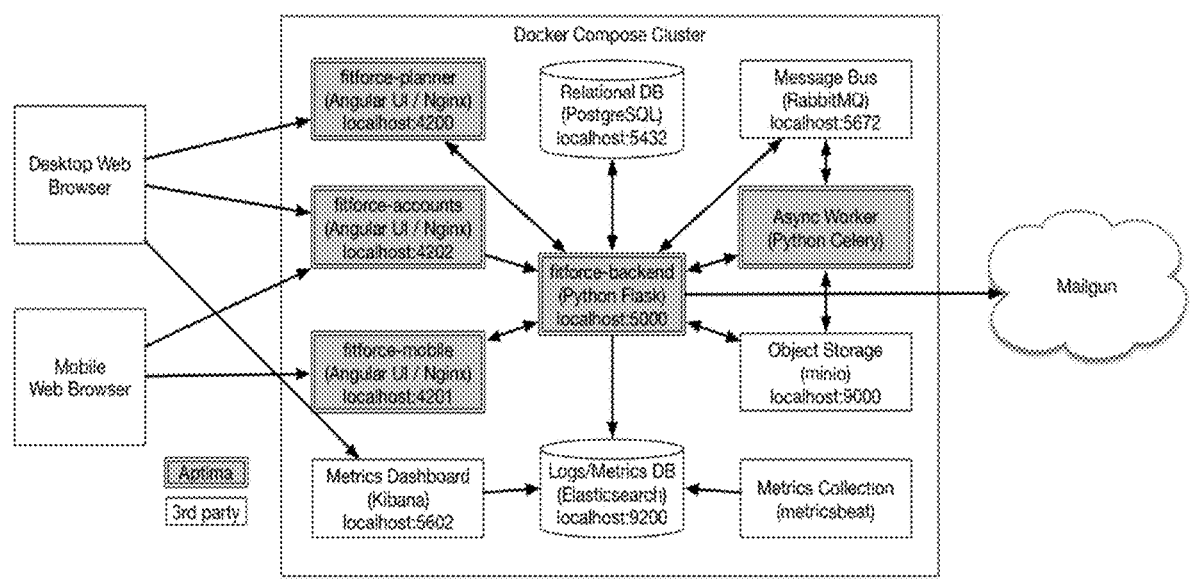
FIG. 9A illustrates one example embodiment of a developer architecture for an example embodiment of an interactive planning system.
Figure 9B:
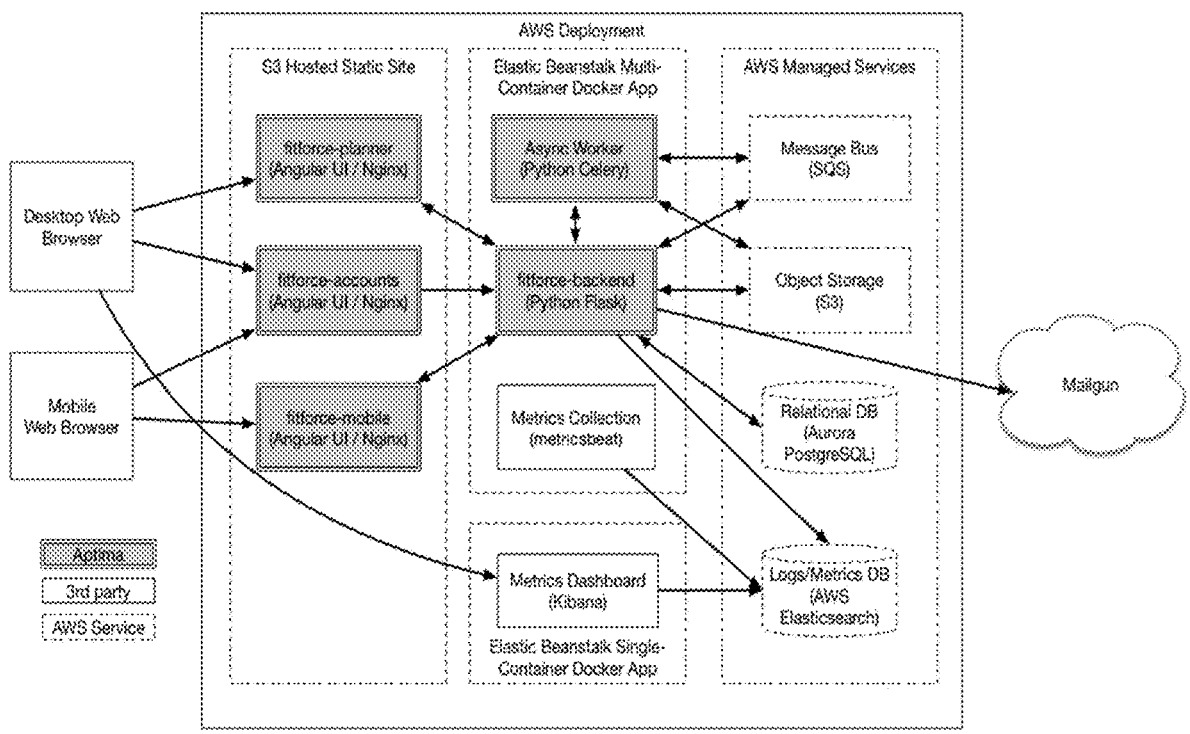
FIG. 9B illustrates on example embodiment of a notional Amazon Web Services (AWS) deployment architecture for an example embodiment of an interactive planning system.

Flexible Architecting for Deployment on DoD Cloud Services. A key challenge for any DoD application development effort is to both adequately support users and promote adoption during the R&D phase, as well as to implement the secure design and robustness that will ease transition efforts to USMC-provisioned infrastructure. In one embodiment, the FitForce components are developed and deployed on Amazon Web Services (AWS) cloud services using standard APIs. As an example, the FitForce planner and mobile applications utilize a scalable PostgreSQL backend through the use of the PostgreSQL REST API. This compatibility allow the system to leverage various managed database service offerings by leading providers such as AWS, which offers its Relational Database Service (RDS) with Aurora/PostgreSQL engines, and Microsoft's Azure Database for PostgreSQL. FIGS. 9A and 9B illustrate the development environment architecture, and a notional AWS architecture that will support use of managed services.

Additionally, the FitForce planner system supports several performance requirements to include the following:

Support all REST API calls with an average response time<500 ms when under high load;
Support 1,000 planning users and 10,000 mobile trainees;
Scale elastically at the service and database level
Support incremental nightly data backups;
Support long-running tasks with an asynchronous API;
Support allowing unauthenticated users to create a new user;
Integrate with an external mail system to send notification/password reset emails to user;
Maintain automated unit and integrations test suites from the beginning of development;
Capture performance telemetry; and
Ship log messages to an aggregator.

In addition, in order to support adaptations to our architecture over time as requirements change, the FitForce system complies with an Event Sourcing architecture pattern. This pattern specifies that the primary persistence for the system will be an immutable event log, and then all reads and analytics will be performed on derivative read models or specialized analytics databases.

Integration with External Capabilities for Assessing User Physiological State. The effectiveness of PT programming can be evaluated using a number of traditional metrics, such as workout sessions completed, or the number of Marines in a unit/across units who are cleared for full duty. However, another metric may be the link between metrics evaluating a user's physical state at a given point in time to the exercises and PT programs delivered to them by FFIs or other plan authors. These user state assessments may be provided by both physiological sensors and subjective responses to questionnaires eliciting contextual considerations such as nutrition, fatigue, pain, and exertion during exercise events. Several promising commercial and GOTS technologies exist (e.g., Smartabase physiological monitoring software) that can augment FFI and AT knowledge about progress against plans, suitable adaptations of those plans, and the appropriateness of the plans for different communities of users.

Physical Training Programming Recommendations. Recommendations related to PT can be implemented in a variety of ways through the FitForce planner and FitForce mobile applications. Each type of recommendation leverages knowledge about physical fitness best practices and, when available, data-driven outcomes to provide unique benefits to end users (e.g., FFIs, individual Marines), stakeholders (e.g., Company Commander), or policymakers (e.g., Force Fitness Readiness Center [FFRC]).

For the individual Marine, who may or may not have a dedicated or available FFI, a variety of vetted fitness plans will be accessible through a FitForce application. Depending on the Marine's desired fitness outcomes (e.g., a First Class score on the Physical Fitness Test [PFT]), the library of available plans will downselect to recommend only those that are capable of progressing the Marine through a series of PT sessions meant to meet his/her specified goal(s). Initially, plans will be created only by knowledgeable professionals (e.g., athletic trainers, rehabilitation/injury prevention experts, strength and conditioning coaches) and trained FFIs. This will limit offerings to those plans that have a higher likelihood of "doing no harm" (i.e., minimizing chance of training-related injuries). Providing plan recommendations through this mechanism will ensure that individual Marines—wherever they are—have access to well-designed, goal-oriented, and safe training programs that they can use at their own discretion to maintain fitness at acceptable or even lethal levels.

For FFIs, who experienced a crash course in physical fitness training best-practices while at the FFRC, the FitForce planner system will provide guiding recommendations during the plan creation process (e.g., recommending more sets/reps for endurance phases but fewer sets/reps for strength or power phases). Additionally, planning recommendations can take the form of providing guidance about which tier or exercises to choose next based on the FFI's stated goal(s) for the overall plan. These planning-process recommendations will provide FFIs with the educational scaffolding they need to maintain (and grow) their knowledge of what constitutes effective and safe PT.

For those who have already decided on their plan, extensive monitoring of individual progress can contribute to recommendations for adjustments to the current plan. Based on assessments of Training Stress Balance (TSB; a measure of the balance between the positive function of fitness and the negative function of fatigue), adjustments may scale back the planned intensity (or load or volume) or swap a more advanced exercise for a similar but beginner or intermediate version (i.e., a regression exercise) to thwart injury. Alternatively, adjustments may scale up or increase the difficulty level to maximize individuals' training potentials (always within safe injury-prevention limits). These algorithmic-based recommendations will truly enable individualized physical fitness, while facilitating FFI duties and optimizing the Marine Corps' overall force readiness.

The FitForce planner and mobile applications may also capture activities related to physical fitness planning and execution in combination with survey, sensor, or other ingests from available tools (e.g., Smartabase). This depth of organized data will support the fitness planners as well as Company Commanders as they monitor the physical status of their Marines and oversee the work of the Company FFI (if one exists). For example, ingests from Smartabase on physiological metrics that inform readiness can be provided to the planner to understand the risks of overtraining, or requirements for recovery periods after activities outside of the specific PT context, such as duty-related heavy lifting that may be captured by a sensor. Here these metrics can inform the planning process, leading to exercise mitigations and potentially regressions, or modifications in a plan to maximize performance and reduce injury. Additionally, the FFRC and other groups interested in PT best practices can learn from analyses of these data, especially in terms of plan-related outcomes or training curves' relationship to injuries.

Future Naval Relevance. The FitForce planner system addresses the need for scalable tools for PT programming, execution, and analysis, and creates a sustainable foundation that will make these capabilities available across the Fleet. The overall goal of these efforts is to improve combat readiness, which reflects recent guidance at the highest levels of the Marine Corps and DoD. In particular, the USMC has brought readiness into the front of consciousness through a recent FRAGO highlighting the need for measures to improve Marines' ability to be employed in "any clime and place." Addressing the training injury challenges of the USMC and DoD remains a driving force behind this effort. As an example of the operational need for FitForce tools and concepts, numerous committees have been stood up to research and report on the impact training injuries pose to operational readiness. As stated in the background section, the Military Training Task Force of the Defense Safety Oversight Council (DSOC) has identified an epidemic, where millions of DoD duty days are being lost to preventable injuries and discharges. The DSOC and others offer general recommendations for interventions, but so far, no technology has been developed to evaluate and communicate these in real time, or tailor them for specific situations and users. FitForce Planner is being developed to fill this void and actively combat these challenges.

FitForce Planner, Mobile, and Analytics will result in the following performance improvements:
  Scalable PT planning, execution, and analysis through widely-available, web-based tools;
  Increased collaboration between Marines and the PT resources and personnel supporting their fitness and readiness;
  More efficient structuring and tracking of performance data;
  Data-driven improvement of PT programming through identification of common risk factors and mitigations to reduce risk; and
  Reduction in training-related injuries, based on risk notifications and remediation before an injury occurs.

One Example Embodiment of an Interactive Planning System in Operation:

For illustration purposes and not for limitation, a FitForce planning system will be used to illustrate an example embodiment of an interactive planning system in operation.

Utilizing the FitForce Planning System

When users log in to the FitForce planning system for the first time, they will see a popup notifying them that program resources are being downloaded. This "program resource bundle" includes:
  A complete list of available FFRC-defined exercises (n=555);
  The available PT programming phases (e.g. Hypertrophy, Power) and employment logic;
  The available workout types ("Main Stressors" such as Lower Body, Upper Body Endurance, etc.);
  Stressor-specific tiers and properties;
  Plan levels (Beginner, Intermediate, Advanced);
  The equipment list used for selection during program design;
  The labels for restricted days (e.g. "Weekend", "Holiday", etc.); and
  The user's plan list.

Figure 3A:
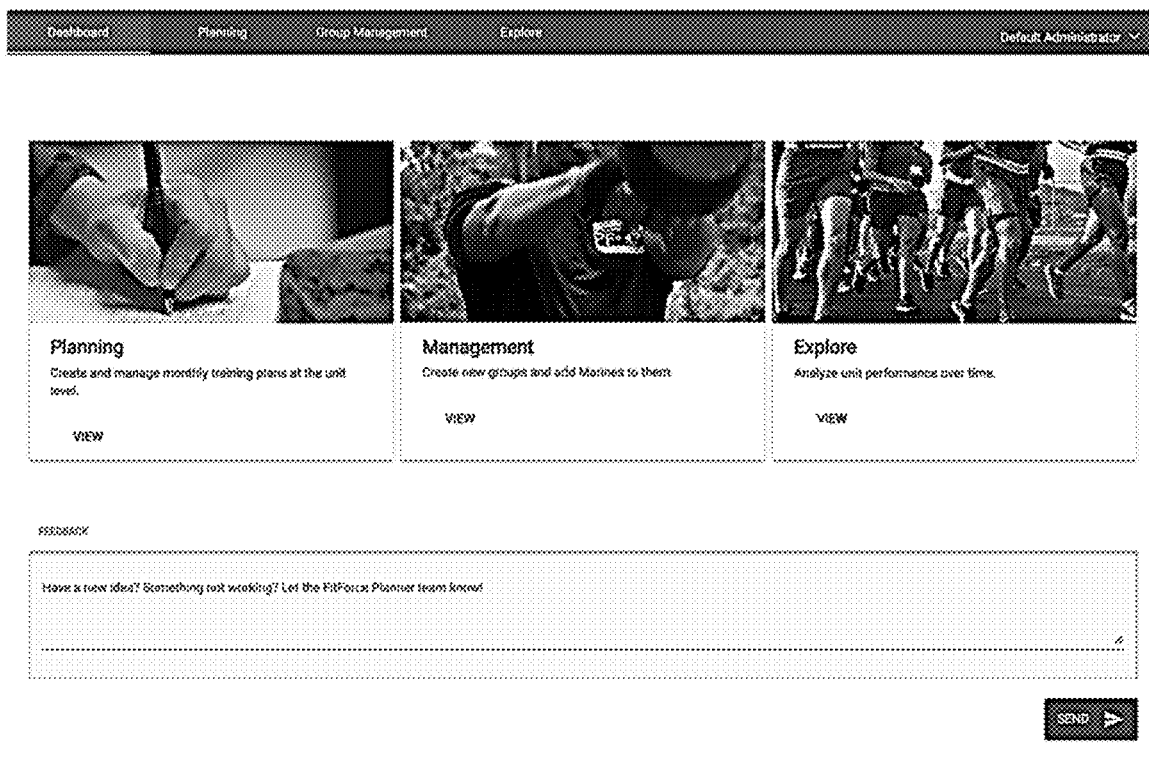

Upon the completion of initial program resource bundle download, users will see the familiar landing page. FIG. 3A illustrates the FitForce planner subsystem landing page. Users can access the Planning, Management (groups), and Explore (statistics) modules, and provide feedback directly from the interface.

Figure 3B:
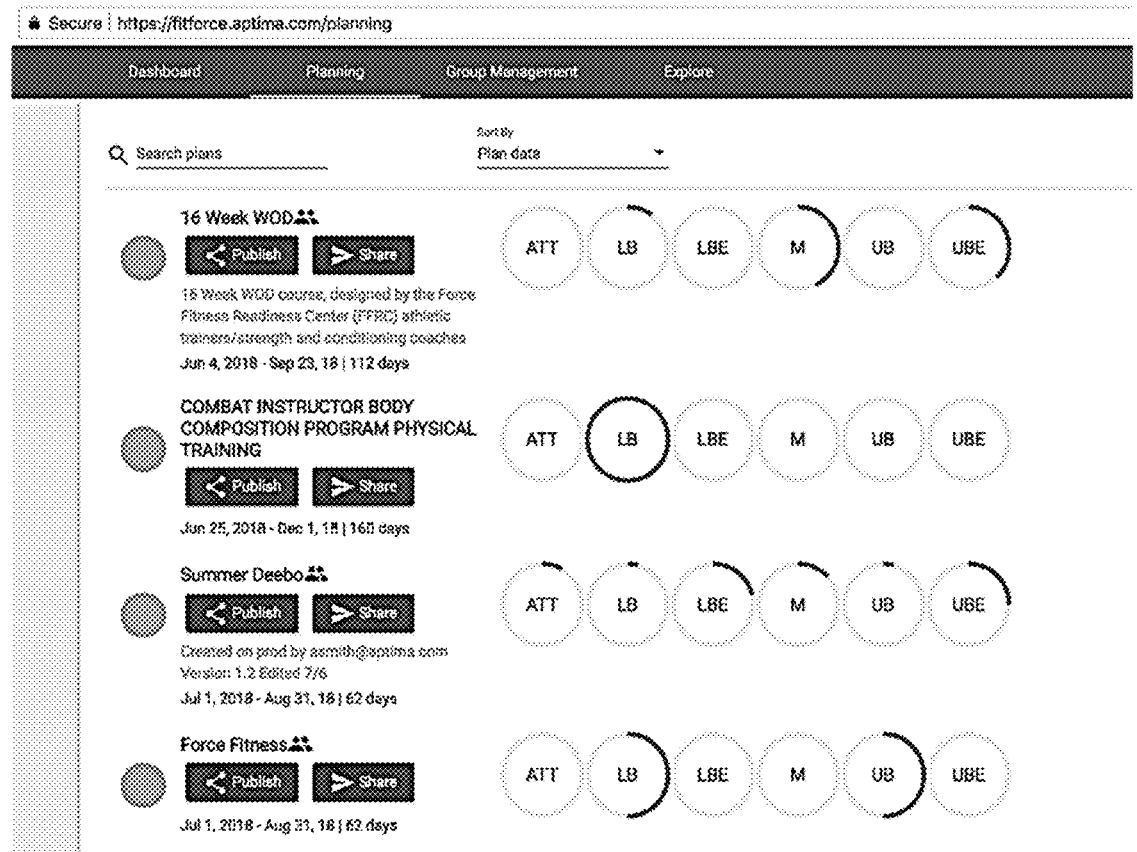

FIG. 3B illustrates the FitForce planner subsystem user interface including the planner library. Individual users can see a list of the plan instances they created, as well as a visualization of the balance of the plan across focus areas. Users can also publish their plans to groups or share the plan with one or more other users for collaborative editing.

When users navigate to the Planning tab, they will see a list of plans they have created, or has been shared with them by other users. In FIG. 3D, the green checkmark icons to the left of the plans denotes that the plan is available for offline use. Orange icons indicate that a plan has been edited, but not yet synced with the cloud server. Users can select any plans they wish to make available for offline use by navigating to the plan details page (">" icon on the right-hand side of the list), where the plan elements will be downloaded to the offline database. The download process writes the following values to the local database:
  Plan days ("Playcards");
  Plan phases; and
  Planned tiers (the bulk of the exercise data is written here).

Figure 3C:
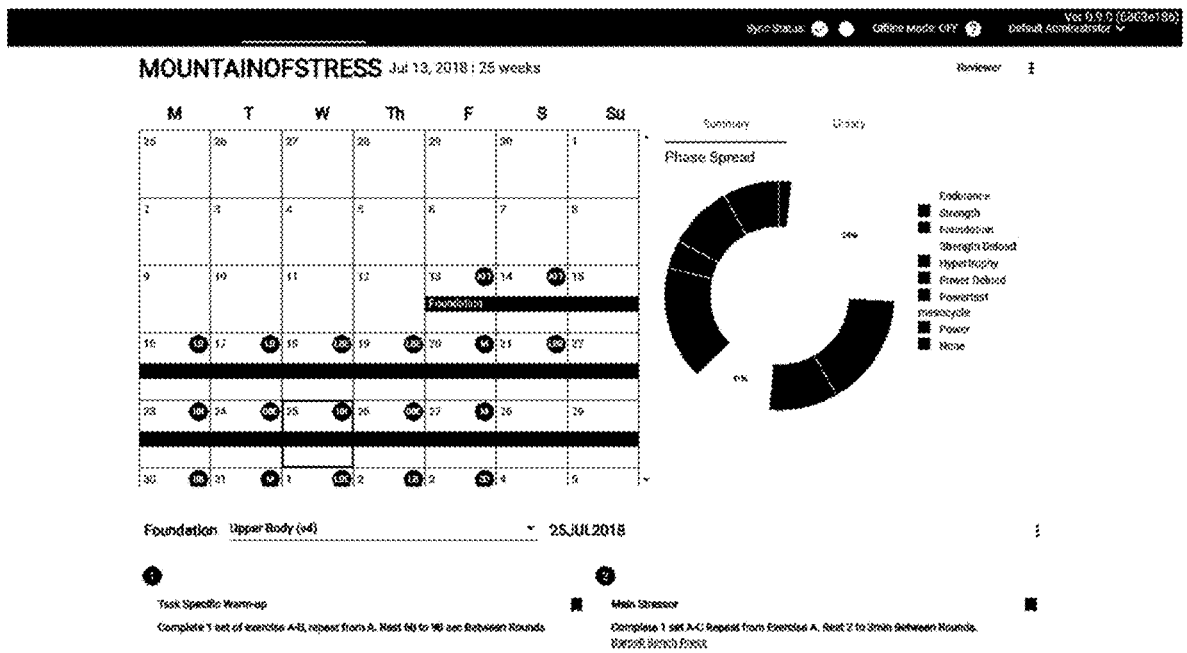
Figure 3D:
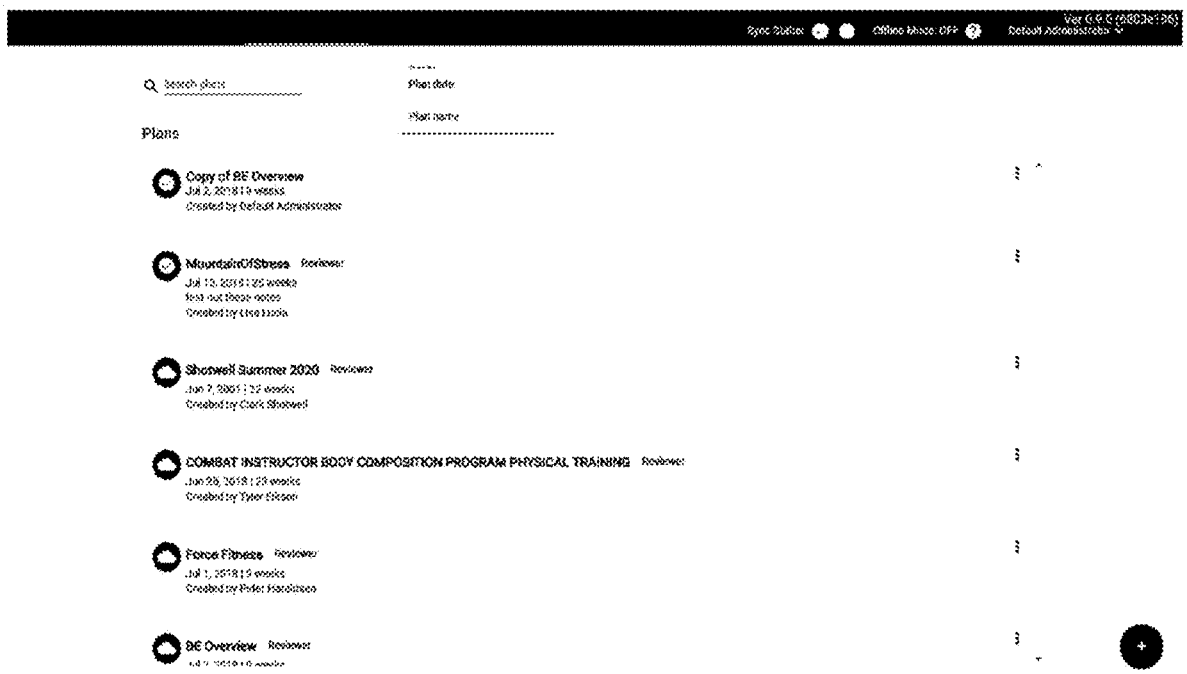

FIG. 3C illustrates Calendar-based planning view, where users can assign specific playcards to dates and view summaries of a playcard's activities. FitForce Planner supports the several main stressors used at the FFRC schoolhouse, including Lower Body (LB), Lower Body Endurance (LBE), Upper Body (UB), Upper Body Endurance (UBE), Agility and Threshold Training (ATT), and Mobility (M). We developed a Custom Day (CD) that supports any number of exercises and tiers.

In FIG. 3D, the checkmark icons to the left of the plans denotes that the plan is available for offline use. Different color icons may be used to indicate that a plan has been edited, but not yet synced with the cloud server. Users can select any plans they wish to make available for offline use by navigating to the plan details page (">" icon on the right-hand side of the list), where the plan elements will be downloaded to the offline database.

FIG. 3E illustrates Playcard creation and editing interface. Users can select from a standardized list of ~550 exercises, organized by main stressor and tier. Users receive guidance (in red) when they specify sets/reps/loads that are outside the FFRC guidance for a specific phase/stressor combination. They are walked through playcard creation in a tier-based, step-by-step workflow that results in a "Complete" playcard that can be published to other users.

FIG. 3F illustrates how exercises specified for a playcard are represented in the user interface. The examples show a playcard tier for Upper Body Endurance activity. The tier is filled out using the dropdown menus.

Figure 3G:
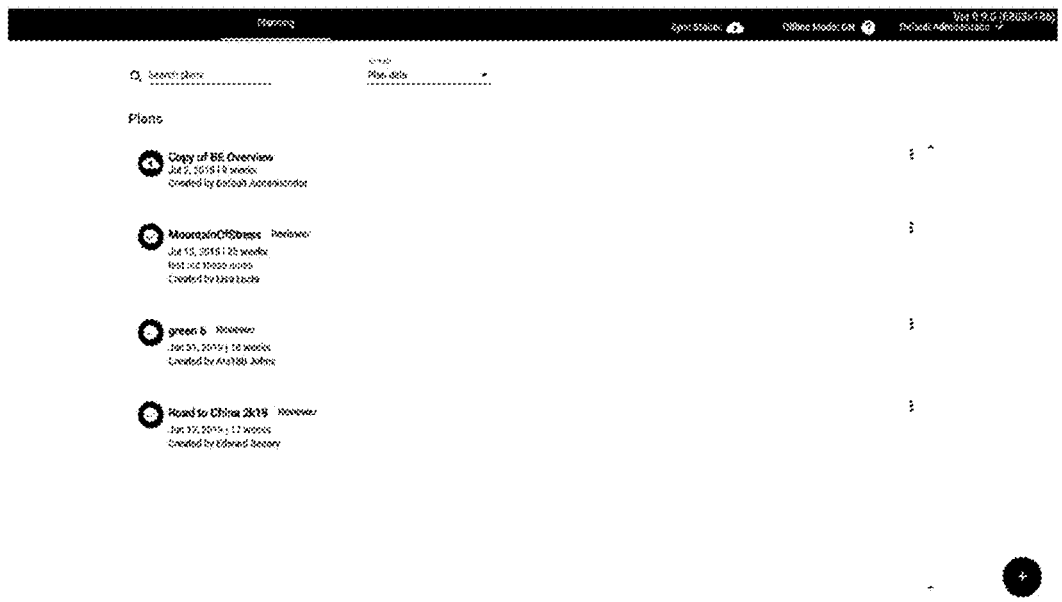

FIG. 3G illustrates when transitioning into an offline state, users can continue to edit any plans that where data are available in the local database. FIG. 3G shows 1) how the user is notified that he/she is now operating in an offline state; 2) plans not available for editing are grayed out; and 3) Group Management and Explore tabs are disabled. Plan list when in offline mode. Users can see an icon at the top of the screen notifying them that they are operating offline, while unavailable plans and features are grayed out.

When the application reenters a connected state, it can be synchronized with the FitForce planner subsystem operating in Amazon Web Services GovCloud. Users may be notified of this process or users will be able to continue working while the application syncs in the background.

Figure 3H:

FIG. 3H illustrates group creation and management interface. Users can create groups, add existing system users, or invite new users via email. Groups are the primary method for publishing and sharing plans to be executed.

In some embodiments, user profile management on the planner subsystem and mobile subsystem may comprise the following:

One-rep max (1RM) inputs to inform individual workout weights during playcard execution;

Inputs and tracking of the results of Individual Physical Assessments (IPAs), Personal Fitness Test (PFT) and Combat Fitness Test (CFT) scores. These scores are assessed by FFIs or ATs, requiring consideration of who will input these values. Testable events as a playcard type, so FFIs or other evaluators would be able to enter these values through the mobile application as they are testing; and Initial Strength Test (IST) results during recruiting, if applicable.

The above elements represent an incomplete list of the personal attributes the FitForce planner system may track and display for users. The overall intent of these features is to support PT knowledge creation, where these individual data points can be aggregated to individual/group/unit measures of progress and readiness over time.

Figure 2:
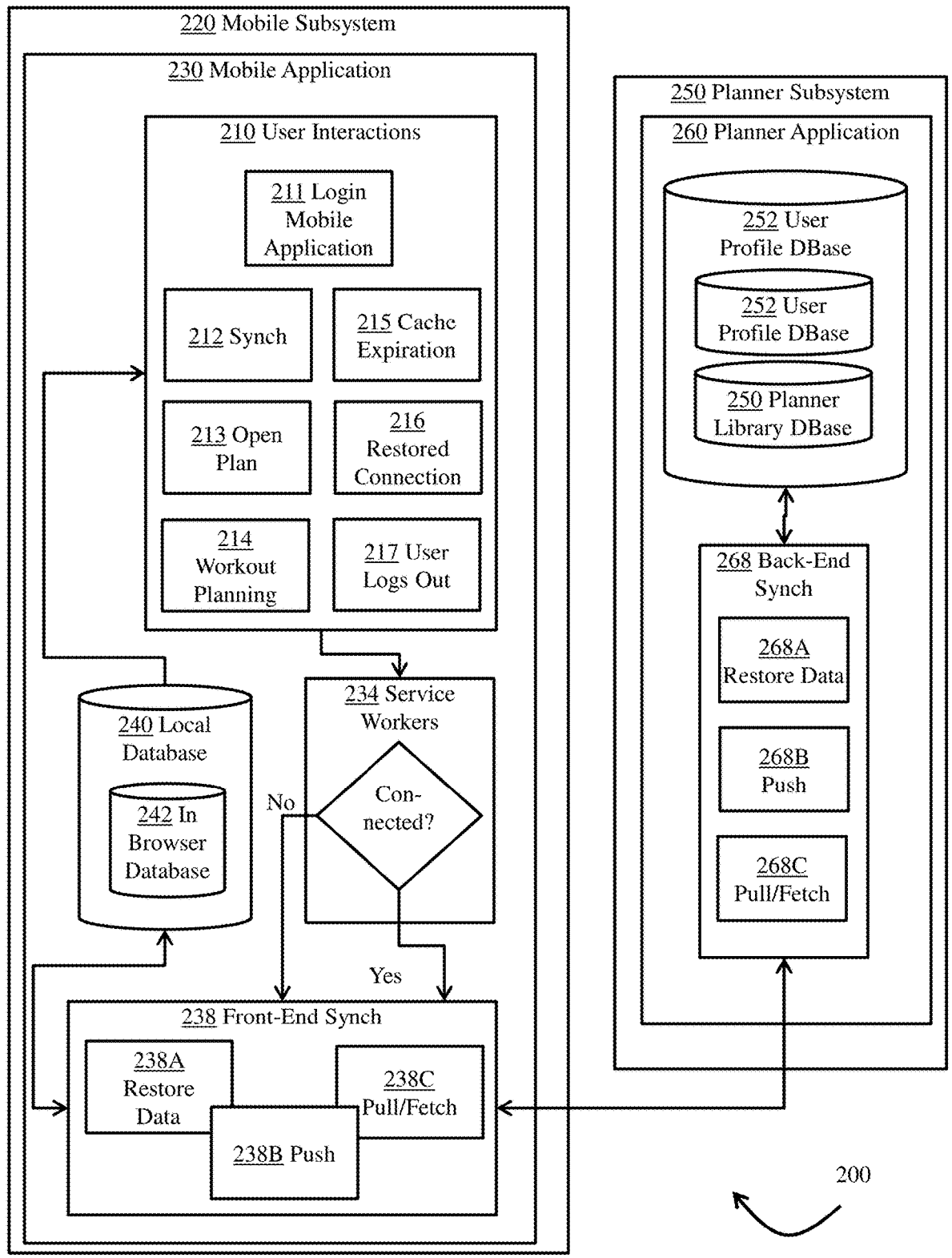
FIG. 2 shows a process diagram illustrating one example embodiment methods of using an interactive planning system.

User Interactions and Synch Actions while Utilizing the FitForce Planning System Referring to FIG. 2 which shows the general process 200 of automatic synching for interactive planning systems based on user interactions 210 using the FitForce planning system as an example. Within the mobile application 230 of the mobile subsystem 220, user interactions 210 generally create actions which use the front-end synch components to access and synchronize data used by the application. Service workers 234 are used to determine where to access the data used by the application. The Service workers 234 determine whether a connection is available to the planner subsystem 250 and planner application 260. If there is a connection, the front-end synch 238 components communicate and perform synch actions with the back-end synch module 268 to update and pull data for use by the mobile application. The synch actions may reflect a full synch that includes all of the synch actions (restore data 238A, push 238B, and pull/fetch 238C) or it may only be a subset of the actions. If there is no connection, the mobile application 230 uses data residing in the local database 240 for user interactions 210. Each of the interactions may generate a separate set of actions to synch and made data available to the application. Examples of user interactions 210 and the actions they generate for synching and making data available to application are described in more detail below.

Login 211. On login 211, the FitForce Planner executes a full synch with the front-end system module 238. The full synch pushes 238B any pending updates to the planner application 260, pulls 238C new data from the planner application 260, restores data 238A in the local database 240, and refreshes the data displayed in the FitForce Planner mobile application 230. This will catch any cached entity expiration that may have occurred since the user has last logged on. If these data/plans were not shared with another user by using the FitForce Planner, they may be removed from the database on login 211. For the situation of login 211, the synch actions automatically perform a full synch. The synch actions to perform: Push 238B+Pull 238C +Restore Data 238A.

Synch 212. Synch 212 represents a manually initiated set of synch actions through a user interaction 210 with the front-end synch module 238. Depending on connectivity or data locations, a synch 212 may be a full synch or it may be a partial synch only performing a subset of the synch actions in the front-end synch module. For the situation of a manual full synch 212, consistent with the synch actions on login 211, the synch actions automatically perform a full synch. The synch actions to perform: Push 238B+Pull/Fetch 238C+Restore Data 238A.

Open 213 an Unavailable Offline Plan. When a user has a connection to the planner application 260 and they open a plan 213 that is not available in the local database 240, plan resources and planning data should be pulled from the planner application server 252 and stored in the client's browser/mobile application local database 240. This situation could be encountered if a user is using a new browser, has cleared their browsing data, or if they are opening a shared plan for the first time. For the situation of opening 213 an unavailable offline plan, the synch actions to perform: Pull/Fetch 238C+Restore Data 238A.

Open 213 an Available Offline Plan. When a user opens 213 a plan that they have previously downloaded to the local database 240, plan resources that are stored in the local database 240 should be used and plan resources and data that are cached should be pulled from the local database 240 and stored in the browser database 242. In this situation, the service worker 234 recognizes the requested plan being available in the local database 240 and pulls it the plan for the user. This is similar to the situation when the user is using the mobile application 230 without connectivity to the planner application 260. In an unconnected situation, the service workers 234 recognize the lack of a connection and performs synch actions with the local database 240. For the situation of a user opening an available offline plan, whether connected or not connected, the synch actions to perform: Pull 238C+Restore Data 238A (local to mobile application 230).

Workout Planning 214. The below example user interactions lead to automatic synch actions so that the user does not lose any data if they were to go offline and be unable to re-establish a connection:

Create, mark complete, or delete a plan day (standard or custom);

Create, update, or delete a phase (standard or custom);

Finish creating or updating a plan (clicked the "Check" button);

Delete a plan;

Finish planning a day (clicked "Review" button); and

Focus on the workout planning component is lost (user clicks away).

A synch action may occur when any change is made to a planned exercise or tier, or only when the user has completed planning or clicked away. For the above situations, the synch actions to perform: Push 238B (only the changed entities and any dependent entities involved).

Cache Expiration 215. While the Planner is in use, it should periodically check if any cached entities have expired and notify the user that they need to refresh their planning data. Only entities that are not cached and have expired will be pulled. For the situation of cache expiration, the synch actions to perform: Pull 238C+Restore Data 238A.

Restored Connection 216. If the user is having connectivity issues, the mobile application 230 designates the user to be offline and will not perform any automatic synch actions until a connection has been restored. Once a reliable connection has been established to the back-end synch module 268, the user should be notified that their connection has been restored and be prompted to save their work and refresh their planning data. For the situation of restored connection, the synch actions to perform: Push 238B+Pull/Fetch 238C+Restore Data 238A (full synch).

User Navigates Away or Logs Out 217. If the user is online and attempts to navigate away from the site or close the browser and has unsaved data, the application can notify the user that they need to save their work to ensure they don't lose any data. For the situation of a user navigating away or logging out, the synch actions to perform: Push 238B or periodic full synch (Push 238B+Pull/Fetch 238C+ Restore Data 238A).

Figure 10B:
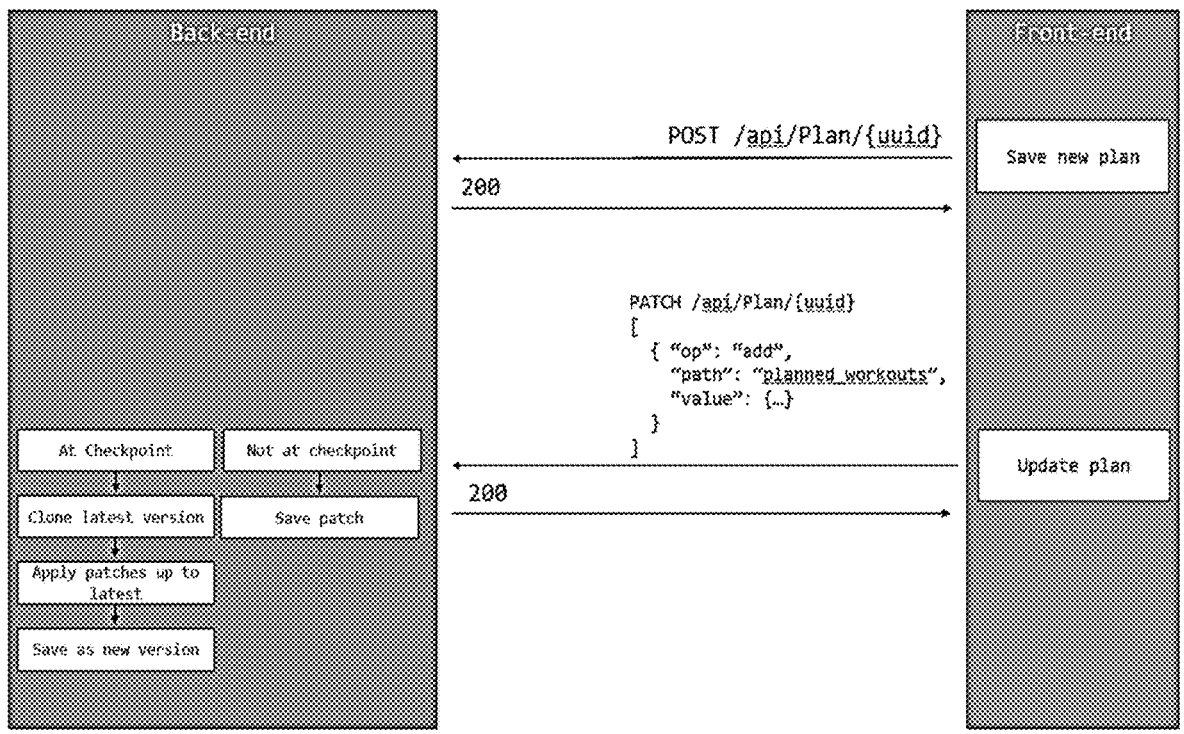
FIG. 10B shows an example of the data flow when using JSONPatch to create or update a plan document.
Figure 10C:
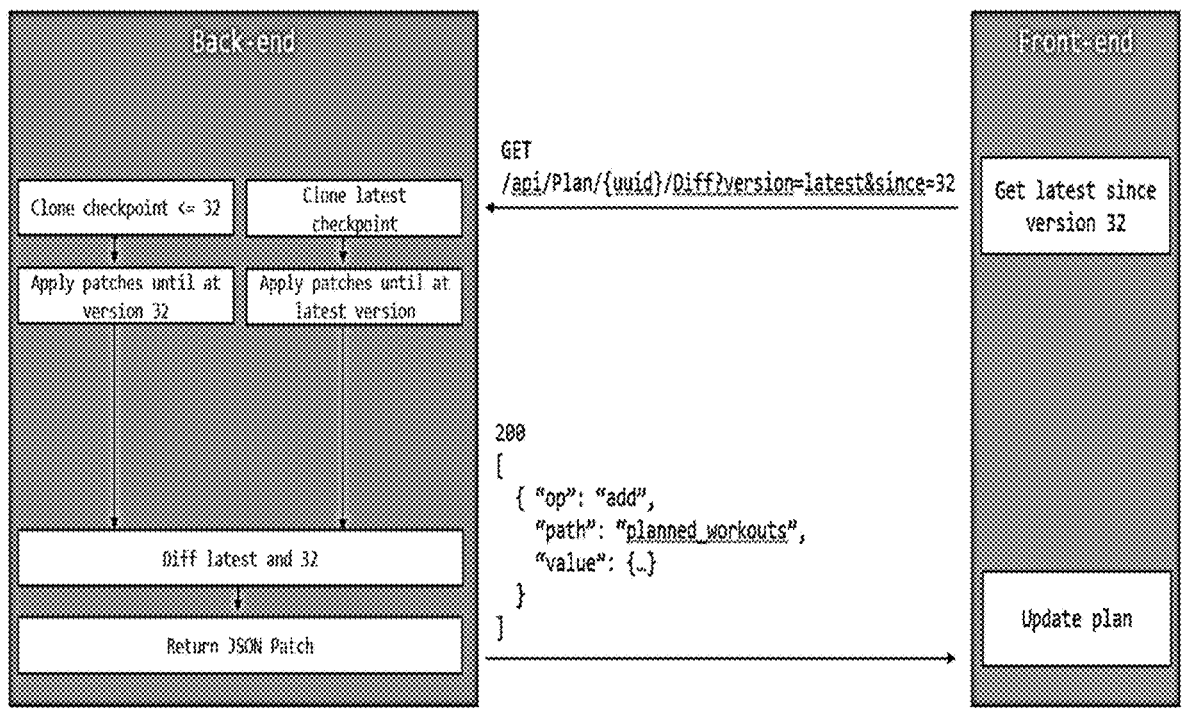
FIG. 10C shows an example of the data flow for updating/versioning an existing plan.

Consistent with the above actions, FIGS. 10A-10C show use of the JSON document structure to synch workout plans between the front-end synch module and the back-end synch module. FIG. 10A shows an example of the JSON document structure for a workout plan. FIG. 10B shows the data flow when using JSONPatch to create or update a plan document. For creating a plan: Front-end provides JSON plan document and Back-end stores document. For updating a plan: Front-end generates a JSON Patch payload; Back-end saves a version of the plan if at a checkpoint, else it saves the patch only; and Checkpoint frequency is a tune-able configuration parameter that dictates the frequency at which a version of a document is saved. FIG. 10C shows the data flow for updating/versioning an existing plan: Front-end requests latest changes since a version; Back-end utilizes stored patches and checkpoints to generate a diff of the versions; and Returns diff as JSON Patch.

One Embodiment of an Interactive Planning System implemented in a Software Program Product Executed by a Processor Based System As will be readily apparent to those skilled in the art, one embodiment of the systems and methods for fitness planning can be embodied in hardware, software, or a combination of hardware and software. For example, a computer system or server system, or other computer implemented apparatus combining hardware and software adapted for carrying out the methods described herein, may be suitable. One embodiment of a combination of hardware and software could be a computer system with a computer program that, when loaded and executed, carries out the respective methods described herein. In some embodiments, a specific use computer, containing specialized hardware or computer programming for carrying out one or more of the instructions of the computer program, may be utilized. In some embodiments, the computer system may comprise a device such as, but not limited to a digital phone, cellular phone, laptop computer, desktop computer, digital assistant, server or server/client system.

Computer program, software program, program, software or program code in the present context mean any expression, in any language, code or notation, of a set of instructions readable by a processor or computer system, intended to cause a system having an information processing capability to perform a particular function or bring about a certain result either directly or after either or both of the following: (a) conversion to another language, code or notation; and (b) reproduction in a different material form. A computer program can be written in any form of programming language, including compiled or interpreted languages, and it can be deployed in any form, including as a stand-alone program or as a module, component, subroutine, or other unit suitable for use in a computing environment.

Figure 13:
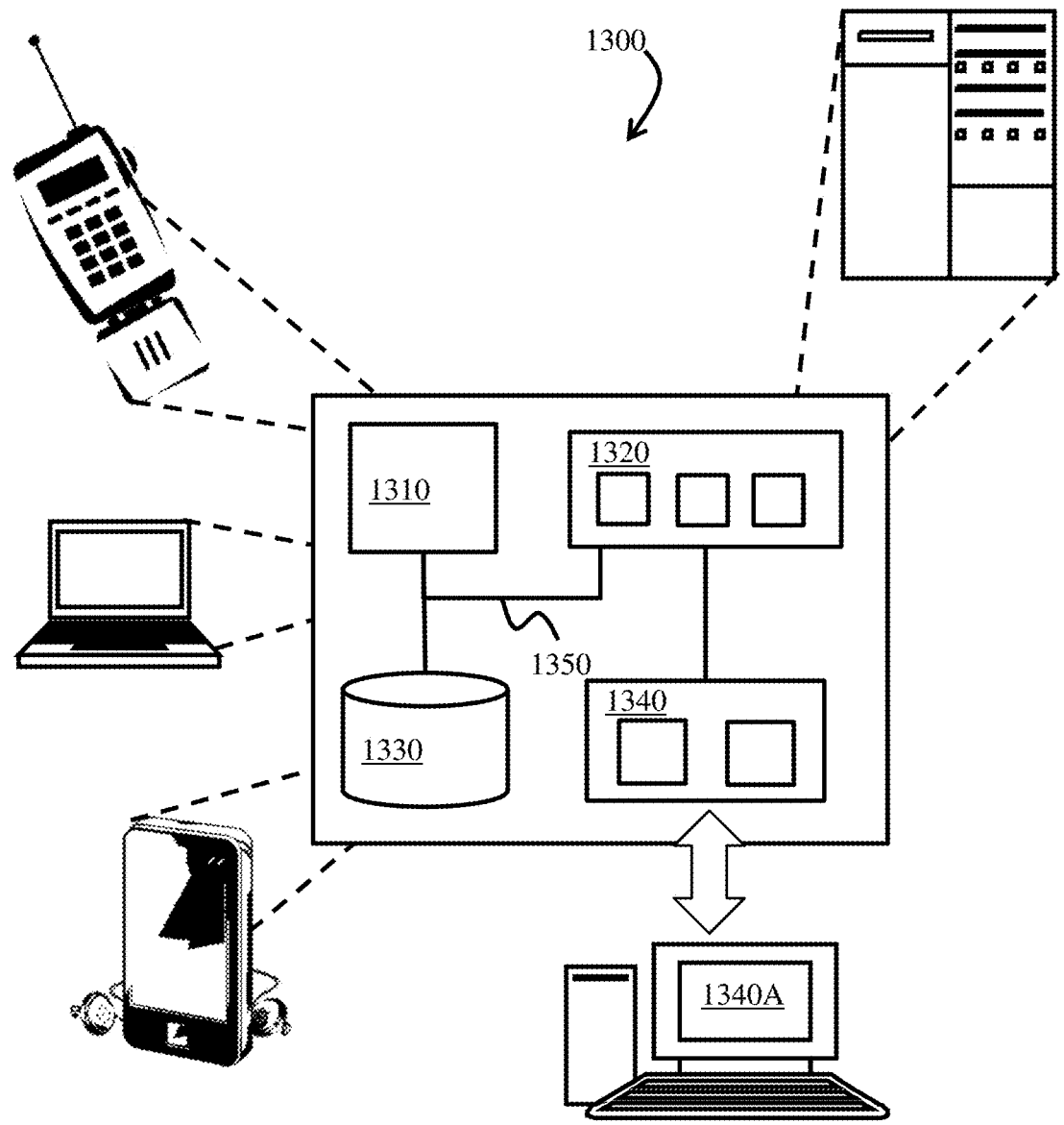
FIG. 13 illustrates one example embodiment of a computer system suitable for an interactive planning system.

FIG. 13 is a schematic diagram of one embodiment of a computer system 1300 by which the environmental system reaction methods may be carried out. The computer system 1300 can be used for the operations described in association with any of the computer implemented methods described herein. The computer system 1300 includes at least one processor 1310, a memory 1320 and an input/output device 1340. Each of the components 1310, 1320, and 1340 are operably coupled or interconnected using a system bus 1350. The computer system 1300 may further comprise a storage device 1330 operably coupled or interconnected with the system bus 1350.

The processor 1310 is capable of receiving the instructions and/or data and processing the instructions of a computer program for execution within the computer system 1300. In some embodiments, the processor 1310 is a single-threaded processor. In some embodiments, the processor 1310 is a multi-threaded processor. The processor 1310 is capable of processing instructions of a computer stored in the memory 1320 or on the storage device 1330 to communicate information to the input/output device 1340. Suitable processors for the execution of the computer program instruction include, by way of example, both general and special purpose microprocessors, and a sole processor or one of multiple processors of any kind of computer.

The memory 1320 stores information within the computer system 1300. Memory 1320 may comprise a magnetic disk such as an internal hard disk or removable disk; a magneto-optical disk; an optical disk; or a semiconductor memory device such as PROM, EPROM, EEPROM or a flash memory device. In some embodiments, the memory 1320 comprises a transitory or non-transitory computer readable medium. In some embodiments, the memory 1320 is a volatile memory unit. In another embodiment, the memory 1320 is a non-volatile memory unit.

The processor 1310 and the memory 1320 can be supplemented by, or incorporated in, ASICs (application-specific integrated circuits).

The storage device 1330 may be capable of providing mass storage for the system 1300. In various embodiments, the storage device 1330 may be, for example only and not for limitation, a computer readable medium such as a floppy disk, a hard disk, an optical disk, a tape device, CD-ROM and DVD-ROM disks, alone or with a device to read the computer readable medium, or any other means known to the skilled artisan for providing the computer program to the computer system for execution thereby. In some embodiments, the storage device 1330 comprises a transitory or non-transitory computer readable medium.

In some embodiments, the memory 1320 and/or the storage device 1330 may be located on a remote system such as a server system, coupled to the processor 1310 via a network interface, such as an Ethernet interface.

The input/output device 1340 provides input/output operations for the system 1300 and may be in communication with a user interface 1340A as shown. In one embodiment, the input/output device 1340 includes a keyboard and/or pointing device. In some embodiments, the input/output device 1340 includes a display unit for displaying graphical user interfaces or the input/output device 1340 may comprise a touchscreen. In some embodiments, the user interface 1340A comprises devices such as, but not limited to a keyboard, pointing device, display device or a touchscreen that provides a user with the ability to communicate with the input/output device 1340.

The computer system 1300 can be implemented in a computer system that includes a back-end component, such as a data server, or that includes a middleware component, such as an application server or an Internet server, or that includes a front-end component, such as a client computer having a graphical user interface or an Internet browser, or any combination of them. The components of the system can be connected by any form or medium of digital data communication such as a communication network. Examples of communication networks include, e.g., a LAN, a WAN, wireless phone networks and the computers and networks forming the Internet.

One example embodiment of the interactive planning systems and methods may be embodied in a computer program product, the computer program product comprising a computer readable medium having a computer readable program code tangibly embodied therewith, the computer program code configured to implement the methods described herein, and which, when loaded in a computer system comprising a processor, is able to carry out these methods.

Although this invention has been described in the above forms with a certain degree of particularity, it is understood that the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention which is defined in the claims and their equivalents.

References

The publication and other material used herein to illuminate the invention or provide additional details respecting the practice of the invention, are incorporated be reference herein, and for convenience are provided in the following bibliography.

Citation of the any of the documents recited herein is not intended as an admission that any of the foregoing is pertinent prior art. All statements as to the date or representation as to the contents of these documents is based on the information available to the applicant and does not constitute any admission as to the correctness of the dates or contents of these documents.

Bullock, S. H., Jones, B. H., Gilchrist, J., & Marshall, S. W. (2010). Prevention of physical training—related injuries: recommendations for the military and other active populations based on expedited systematic reviews. Am J Prev Med, 38(1), S156-S181.

Hauret, K. G., Jones, B. H., Bullock, S. H., Canham-Chervak, M., & Canada, S. (2010). Musculoskeletal injuries: description of an under-recognized injury problem among military personnel. Am J Prev Med, 38(1), S61-S70.

US Army. (2011). "Prevention and Control of Musculoskeletal Injuries Associated with Physical Training." Technical Bulletin Medical (TB MED) 592.

Altarac, M., Gardner, J. W., Popovich, R. M., Potter, R., Knapik, J. J., & Jones, B. H. (2000). Cigarette smoking and exercise-related injuries among young men and women. Am J Prev Med, 18(3), 96-102.

Progressive Web Apps. Accessed 20 Sept 2018 at https://developers.google.com/web/progressive-web-apps/.

Web App Manifest. Accessed 20 Sept 2018 at https://developer.mozilla.org/en-US/docs/Web/Manifest.

Relational Database Service. Accessed 20 Sept 2018 at https://aws.amazon.com/rds/.

PostgreSQL for Azure. Accessed 20 Sept 2018 at https://docs.microsoft.com/en-us/azure/postgresql/overview.

Twelve Factor App Principles. Accessed 20 Sept 2018 at https://12factor.net/.

Event Sourcing. Accessed 20 Sept 2018 at https://martinfowler.com/eaaDev/EventSourcing.html.

Offline Storage for Progressive Web Apps. Accessed 20 Sept 2018 at https://developers.google.com/web/fundamentals/instant-and-offline/web-storage/offline-for-pwa Angular. Accessed 20 Sept 2018 at https://angular.io/.

Apps that Work Natively on the Web and Mobile. Accessed 20 Sept 2018 at https://blog.angular.io/apps-that-work-natively-on-the-web-and-mobile-9b26852495e7.

Fragmentary Order 4 (Implementation) to MARINE CORPS FORCE INTEGRATION CAMPAIGN PLAN. Accessed 20 Sept 2018 at https://www.defense.gov/Portals/1/Documents/pubs/WISR_Implementation_Plan_USMC.pdf.

Establishment of the Secretary of Defense Close Combat Lethality Task Force Memo (2018FEB08).

(DTM)-18-001 Establishment of the Secretary of Defense Close Combat Lethality Task Force (2018 MAR 16), Attachment 2, 7.b.2.

Cross, M. J., Williams, S., Trewartha, G., Kemp, S. P. T., & Stokes, K. A. (2016). The Influence of In-Season Training Loads on Injury Risk in Professional Rugby Union.

International Journal of Sports Physiology and Performance, 11(3), 350-355. https://doi.org/10.1123/ijspp.2015-0187.

Gabbett, T. J., Hulin, B. T., Blanch, P., & Whiteley, R. (2016). High training workloads alone do not cause sports injuries: how you get there is the real issue. Br J Sports Med, 50(8), 444-445. https://doi.org/10.1136/bjsports-2015-095567.

Hulin, B. T., Gabbett, T. J., Blanch, P., Chapman, P., Bailey, D., & Orchard, J. W. (2014). Spikes in acute workload are associated with increased injury risk in elite cricket fast bowlers. Br J Sports Med, 48(8), 708-712. https://doi.org/10.1136/bjsports-2013-092524.

We claim:

1. A processor based interactive planning system comprising:

a planner subsystem;

a mobile subsystem;

the planner subsystem comprising a user profile database, a planner library database and a back-end synch module;

the mobile subsystem comprising a mobile device and a mobile application;

the mobile application comprising a browser application, a user interface, an in-browser database, and a front-end synch module;

the user profile database having a mobile program resource entity;

the planner library database having a planner program resource entity corresponding to the mobile program resource entity;

the mobile application configured to update the mobile program resource entity to an updated mobile program resource entity based on a user interaction with the mobile application;

the front-end synch module configured to be in intermittent communication with the back-end synch module;

whereby when the front-end synch module is not in communication with the back-end synch module, the mobile application is configured to store the updated mobile program resource entity in the in-browser database;

whereby when the front-end synch module is in communication with the back-end synch module, the mobile application is configured to perform a synch and synchronize the planner program resource entity with the updated mobile program resource entity; wherein the updated mobile program resource entity comprises a file configured in a JSON (JavaScript Object Notation) document structure; wherein the in-browser database is configured with a JSON Patch schema; wherein the planner library database is configured with a JSON Patch schema; and whereby the synch of the planner program resource entity with the updated mobile program resource entity communicates a patch of the undated mobile program resource entity between the front-end synch module and the back-end synch module to update the planner library database.

2. The processor based interactive planning system of claim 1 wherein the mobile application further comprises:
a service worker module configured to determine whether the front-end synch module is in communication with the back-end synch module;
whereby when the front-end synch module is not in communication with the back-end synch module, the service worker module is configured to store the updated mobile program resource entity in the in-browser database; and
whereby when the front-end synch module is in communication with the back-end synch module, the service worker module is configured to communicate the updated mobile program resource entity with the front-end synch module to perform the synch and synchronize the planner program resource entity with the updated mobile program resource entity.

3. The processor based interactive planning system of claim 2 wherein:
the user interaction comprises a login; and
when the front-end synch module is in communication with the back-end synch module, the front-end synch module is configured to execute the synch with the back-end synch module and synchronize the mobile program resource entity with the planner program resource entity.

4. The processor based interactive planning system of claim 2 wherein when the front-end synch module at a first time is not in communication with the back-end synch module and the front-end synch module at a subsequent time is in communication with the back-end synch module, the front-end synch module is configured to execute the synch with the back-end synch module and synchronize the planner program resource entity with the updated mobile program resource entity.

5. The processor based interactive planning system of claim 2 wherein:
the user interaction comprises a request to pull the mobile program resource entity; and
the service worker module is configured to pull the mobile program resource entity from the in-browser database.

6. The processor based interactive planning system of claim 2 wherein:
the user interaction comprises a request to pull the mobile program resource entity; and
when the mobile program resource entity is in the in-browser database, the service worker module is configured to pull the mobile program resource entity from the in-browser database; and
when the mobile program resource entity is not in the in-browser database and the front-end synch module is in communication with the back-end synch module, the service worker module is configured to pull the planner program resource entity from the planner library database as the mobile program resource entity.

7. The processor based interactive planning system of claim 2 wherein:
the mobile application is a fitness application;
the mobile program resource entity comprises a fitness plan; and
the mobile device comprises a smartphone.

8. The processor based interactive planning system of claim 7 wherein the fitness plan comprises a video file.

9. The processor based interactive planning system of claim 1 wherein the synch of the planner program resource entity with the updated mobile program resource entity communicates a patch of the updated mobile program resource entity between the front-end synch module and the back-end synch module to update the planner library database.

10. The processor based interactive planning system of claim 1 wherein:
the synch of the planner program resource entity with the updated mobile program resource entity communicates a patch of the updated mobile program resource entity from the in-browser database between the front-end synch module and the back-end synch module to update the planner library database.

11. The processor based interactive planning system of claim 1 wherein:
the mobile application is a fitness application;
the mobile program resource entity comprises a fitness plan;
the updated mobile program resource entity comprises an updated fitness plan;
the mobile device comprises a smartphone; and
the synch of the fitness plan with the updated fitness plan communicates a patch of the updated fitness plan from the in-browser database between the front-end synch module and the back-end synch module to update the planner library database.

12. A processor based interactive planning system comprising:
a planner subsystem;
a mobile subsystem;
the planner subsystem comprising a user profile database, a planner library database and a back-end synch module;
the mobile subsystem comprising a mobile device and a mobile application, the mobile application comprising a browser application, a user interface, an in-browser database, and a front-end synch module;
the user profile database having a mobile program resource entity;
the planner library database having a planner program resource entity corresponding to the mobile program resource entity;
the mobile application configured to update the mobile program resource entity to an updated mobile program resource entity based on a user interaction with the mobile application;
the front-end synch module configured to be in intermittent communication with the back-end synch module;
whereby when the front-end synch module is not in communication with the back-end synch module, the mobile application is configured to store the updated mobile program resource entity in the in-browser database;
whereby when the front-end synch module is in communication with the back-end synch module, the mobile application is configured to perform a synch and synchronize the planner program resource entity with the updated mobile program resource entity; wherein the mobile application is a fitness application; wherein the mobile program resource entity comprises a fitness plan video configured in a JSON (JavaScript Object Notation) document structure; wherein the mobile device comprises a smartphone; the updated mobile program resource entity comprises an updated fitness plan video configured in a JSON document structure; wherein the in-browser database is configured with a JSON Patch schema; wherein the planner library database is configured with a JSON Patch schema;

and whereby the synch of the fitness plan video with the updated fitness plan video communicates a patch of the updated fitness plan between the front-end synch module and the back-end synch module to update the planner library database.

13. The processor based interactive planning system of claim 12 wherein the mobile application further comprises:
a service worker module configured to determine whether the front-end synch module is in communication with the back-end synch module;
whereby when the front-end synch module is not in communication with the back-end synch module, the service worker module is configured to store the updated mobile program resource entity in the in-browser database; and
whereby when the front-end synch module is in communication with the back-end synch module, the service worker module is configured to communicate the updated mobile program resource entity with the front-end synch module to perform the synch and synchronize the planner program resource entity with the updated mobile program resource entity.

14. The processor based interactive planning system of claim 13 wherein:
the user interaction comprises a login; and
when the front-end synch module is in communication with the back-end synch module, the front-end synch module is configured to execute the synch with the back-end synch module and synchronize the mobile program resource entity with the planner program resource entity.

15. The processor based interactive planning system of claim 13 wherein when the front-end synch module at a first time is not in communication with the back-end synch module and the front-end synch module at a subsequent time is in communication with the back-end synch module, the front-end synch module is configured to execute the synch with the back-end synch module and synchronize the planner program resource entity with the updated mobile program resource entity.

16. The processor based interactive planning system of claim 13 wherein:
the user interaction comprises a request to pull the mobile program resource entity; and
the service worker module is configured to pull the mobile program resource entity from the in-browser database.

17. The processor based interactive planning system of claim 13 wherein:
the user interaction comprises a request to pull the mobile program resource entity; and
when the mobile program resource entity is in the in-browser database, the service worker module is configured to pull the mobile program resource entity from the in-browser database; and
when the mobile program resource entity is not in the in-browser database and the front-end synch module is in communication with the back-end synch module, the service worker module is configured to pull the planner program resource entity from the planner library database as the mobile program resource entity.

18. The processor based interactive planning system of claim 13 wherein:
the mobile application is a fitness application;
the mobile program resource entity comprises a fitness plan; and
the mobile device comprises a smartphone.

19. The processor based interactive planning system of claim 1 wherein the synch of the planner program resource entity with the updated mobile program resource entity communicates a patch of the updated mobile program resource entity between the front-end synch module and the back-end synch module to update the planner library database.

20. The processor based interactive planning system of claim 1 wherein the synch of the planner program resource entity with the updated mobile program resource entity communicates a patch of the updated mobile program resource entity from the in-browser database between the front-end synch module and the back-end synch module to update the planner library database.

* * * * *